US011931434B2

(12) United States Patent
Kajiwara et al.

(10) Patent No.: US 11,931,434 B2
(45) Date of Patent: Mar. 19, 2024

(54) OIL-IN-WATER TYPE SUNSCREEN COSMETIC

(71) Applicant: KAO CORPORATION, Tokyo (JP)

(72) Inventors: Keigo Kajiwara, Setagaya-ku (JP);
Shinichi Tsukii, Koshigaya (JP);
Shingo Hirono, Cincinnati, OH (US);
Takuji Enomoto, Edogawa-ku (JP)

(73) Assignee: KAO CORPORATION, Tokyo (JP)

( * ) Notice: Subject to any disclaimer, the term of this patent is extended or adjusted under 35 U.S.C. 154(b) by 498 days.

(21) Appl. No.: 17/279,972

(22) PCT Filed: Sep. 30, 2019

(86) PCT No.: PCT/JP2019/038449
§ 371 (c)(1),
(2) Date: Mar. 25, 2021

(87) PCT Pub. No.: WO2020/067561
PCT Pub. Date: Apr. 2, 2020

(65) Prior Publication Data
US 2022/0031582 A1 Feb. 3, 2022

(30) Foreign Application Priority Data

Sep. 28, 2018 (JP) ................................ 2018-185468

(51) Int. Cl.
*A61K 8/06* (2006.01)
*A61K 8/04* (2006.01)
*A61K 8/891* (2006.01)
*A61Q 17/04* (2006.01)

(52) U.S. Cl.
CPC .............. *A61K 8/062* (2013.01); *A61K 8/042* (2013.01); *A61K 8/891* (2013.01); *A61Q 17/04* (2013.01); *A61K 2800/412* (2013.01); *A61K 2800/596* (2013.01); *A61K 2800/805* (2013.01)

(58) Field of Classification Search
None
See application file for complete search history.

(56) References Cited

U.S. PATENT DOCUMENTS

| 2007/0274943 A1 | 11/2007 | Ishikubo et al. |
| 2010/0209365 A1 | 8/2010 | Takakura et al. |
| 2010/0272763 A1 | 10/2010 | Nakamura |
| 2017/0105909 A1 | 4/2017 | Miyahara et al. |

FOREIGN PATENT DOCUMENTS

| JP | 9-301847 A | 11/1997 |
| JP | 2002-370943 A | 12/2002 |
| JP | 2006-36763 A | 2/2006 |
| JP | 2007-161595 A | 6/2007 |
| JP | 2009-161523 A | 7/2009 |
| JP | 2011-246445 A | 12/2011 |
| JP | 2015-13856 A | 1/2015 |
| JP | 2016-14011 A | 1/2016 |
| JP | 2017-7969 A | 1/2017 |
| JP | 2018-118931 A | 8/2018 |
| TW | I644684 B | 12/2018 |
| WO | WO 2004/103324 A1 | 12/2004 |
| WO | WO 2016204124 | * 12/2016 |

OTHER PUBLICATIONS

International Search Report dated Nov. 26, 2019 in PCT/JP2019/038449 filed on Sep. 30, 2019, citing references AA, AB, and AM-AS therein, 2 pages.
Extended European Search Report & Written Opinion dated May 31, 2022 in European Application No. 19866644.6, citing document AA therein, 10 pages.

* cited by examiner

*Primary Examiner* — Danah Al-Awadi
(74) *Attorney, Agent, or Firm* — Oblon, McClelland, Maier & Neustadt, L.L.P.

(57) ABSTRACT

An oil-in-water type sunscreen cosmetic containing the following component (A) and the following component (B): (A) 1% by mass or more and 40% by mass or less of emulsion particles containing an oil soluble ultraviolet ray absorbent (a1), having an average particle diameter of more than 6 μm and 300 μm or less, and (B) 0.3% by mass or more and 2.5% by mass or less of particles containing an oil soluble ultraviolet ray absorbent (b3) encompassed by an ionic surfactant (b1) and a hydrophobic amphiphilic substance (b2), having a content of a solid oil agent of 2.5% by mass or less based on the total amount of the particles, having an average particle diameter of 6 μm or less.

6 Claims, No Drawings

OIL-IN-WATER TYPE SUNSCREEN COSMETIC

FIELD OF THE INVENTION

The present invention relates to an oil-in-water type sunscreen cosmetic.

BACKGROUND OF THE INVENTION

Sunburn caused by ultraviolet radiation accelerates browning of the skin, decrease of the resilience of the skin, occurrence of wrinkles, and the like, and cosmetics containing an ultraviolet absorbent have been used for preventing these phenomena.

As for an oil-in-water type sunscreen cosmetic, PTL 1 describes that a low viscosity oil-in-water type emulsion composition containing an N-long chain acyl acidic amino acid monosalt capable of forming a gel at ordinary temperature, an amphiphilic substance, water, and an oil is excellent in emulsion stability, pH stability, and the like. The literature also describes a sunscreen lotion as an example of the composition.

PTL 2 describes that an oil-in-water type emulsion skin cosmetic, such as an UV milky lotion, containing an oil agent in a liquid state at 25° C., an oil agent in a solid state or a semisolid state at 25° C., a linear alcohol having 12 to 22 carbon atoms, the prescribed surfactant, and water in the prescribed amounts, having a number average particle diameter of the emulsion particles of 1.0 to 3.0 µm can hide the uneven color of skin and is excellent in use feeling and storage stability.

PTL 3 describes that an ultraviolet ray protection cosmetic containing an ionic surfactant, a hydrophobic amphiphilic substance, a liquid oil agent containing an oil soluble ultraviolet ray absorbent, a solid oil agent, and water in the prescribed amounts, obtained by the prescribed method is excellent in storage stability, ultraviolet ray protection effect, and use feeling, and causes no skin irritation feeling.

CITATION LIST

Patent Literatures

PTL 1: JP 9-301847 A
PTL 2: JP 2015-13856 A
PTL 3: JP 2017-7969 A

SUMMARY OF THE INVENTION

The present invention relates to the following items [1] to [3].

[1] An oil-in-water type sunscreen cosmetic containing the following component (A) and the following component (B):
- (A) 1% by mass or more and 40% by mass or less of emulsion particles containing an oil soluble ultraviolet ray absorbent (a1), having an average particle diameter of more than 6 µm and 300 µm or less, and
- (B) 0.3% by mass or more and 2.5% by mass or less of particles containing an oil soluble ultraviolet ray absorbent (b3) encompassed by an ionic surfactant (b1) and a hydrophobic amphiphilic substance (b2), having a content of a solid oil agent of 2.5% by mass or less based on the total amount of the particles, having an average particle diameter of 6 µm or less.

[2] A method for producing an oil-in-water type sunscreen cosmetic, including the following steps (I) to (III):
- step (I): emulsifying an oil phase containing an oil soluble ultraviolet ray absorbent (a1) in an aqueous medium with an emulsifier, so as to provide an emulsion containing emulsion particles (A) having an average particle diameter of more than 6 µm and 300 µm or less,
- step (II): mixing an ionic surfactant (b1), a hydrophobic amphiphilic substance (b2), an oil soluble ultraviolet ray absorbent (b3), and an aqueous medium under heating for emulsifying, and then cooling at a cooling rate of 0.5° C./sec or more and 10° C./sec or less, so as to provide an emulsion containing particles (B) containing the component (b3) encompassed by the components (b1) and (b2), having an average particle diameter of 6 µm or less, and
- step (III): mixing the emulsion containing the emulsion particles (A) obtained in the step (I) and the emulsion containing the particles (B) obtained in the step (II).

[3] An oil-in-water type sunscreen cosmetic containing the following component (A1) and the following component (B):
- (A1) 1% by mass or more and 40% by mass or less of emulsion particles containing an oil soluble ultraviolet ray absorbent (a1) and a methylphenylpolysiloxane (a3), having an average particle diameter of more than 6 µm and 300 µm or less, and
- (B) 0.3% by mass or more and 5% by mass or less of particles containing an oil soluble ultraviolet ray absorbent (b3) encompassed by an ionic surfactant (b1) and a hydrophobic amphiphilic substance (b2), having a content of a solid oil agent of 2.5% by mass or less based on the total amount of the particles, having an average particle diameter of 6 µm or less.

DETAILED DESCRIPTION OF THE INVENTION

[Oil-in-Water Type Sunscreen Cosmetic]

The oil-in-water type sunscreen cosmetic of the first embodiment of the present invention (which may be hereinafter referred simply to as a "sunscreen cosmetic (1)") contains the following component (A) and the following component (B).

(A) 1% by mass or more and 40% by mass or less of emulsion particles containing an oil soluble ultraviolet ray absorbent (a1), having an average particle diameter of more than 6 µm and 300 µm or less (B) 0.3% by mass or more and 2.5% by mass or less of particles containing an oil soluble ultraviolet ray absorbent (b3) encompassed by an ionic surfactant (b1) and a hydrophobic amphiphilic substance (b2), having a content of a solid oil agent of 2.5% by mass or less based on the total amount of the particles, having an average particle diameter of 6 µm or less The oil-in-water type sunscreen cosmetic of the second embodiment of the present invention (which may be hereinafter referred simply to as a "sunscreen cosmetic (2)") contains the following component (A1) and the following component (B).

(A1) 1% by mass or more and 40% by mass or less of emulsion particles containing an oil soluble ultraviolet ray absorbent (a1) and a methylphenylpolysiloxane (a3), having an average particle diameter of more than 6 µm and 300 µm or less (B) 0.3% by mass or more and 5% by mass or less of particles containing an oil soluble ultraviolet ray absorbent (b3) encompassed by an ionic surfactant (b1) and a hydrophobic amphiphilic substance (b2), having a content of a solid oil agent of 2.5% by mass or less based on the total amount of the particles, having an average particle diameter of 6 μm or less In the following description, the oil-in-water type sunscreen cosmetics of the first embodiment and the second embodiment of the present invention may be collectively referred to as an "(oil-in-water type) sunscreen cosmetic of the present invention".

The sunscreen cosmetic of the present invention can provide a coating film having high uniformity and high water resistance, is excellent in ultraviolet ray protection effect, and has a less sense of burden on the skin and good use feeling thereon, due to the components (A) and (B) or the components (A1) and (B) contained in the prescribed amounts.

In ultraviolet ray absorbents used in a sunscreen cosmetic, an oil soluble ultraviolet ray absorbent has an excellent ultraviolet ray absorbing effect, but in the case where the oil soluble ultraviolet ray absorbent is contained directly in an oil-in-water type sunscreen cosmetic, the oil soluble ultraviolet ray absorbent migrates to the oil phase to decrease the content of the oil soluble ultraviolet ray absorbent in the water phase. Accordingly, in the case where the oil-in-water type sunscreen cosmetic containing the oil soluble ultraviolet ray absorbent is coated on the skin and dried, there is a problem that the dried coating film has fine gaps occurring in the portions where the water phase of the cosmetic exist, and an ultraviolet ray is transmitted through the gaps to fail to provide a sufficient ultraviolet ray protection effect.

For solving the problem, a method of mixing a water soluble ultraviolet ray absorbent in the cosmetic may be considered, but the method has a problem that the water resistance of the coating film of the oil-in-water type sunscreen cosmetic is deteriorated. Furthermore, in the case where the amount of the ultraviolet ray absorbent mixed in the cosmetic is too large, a sense of burden on the skin may occur in coating on the skin, which deteriorates the use feeling.

An issue to be solved by the present invention is to provide an oil-in-water type sunscreen cosmetic that can provide a coating film excellent in uniformity and water resistance, can provide an excellent ultraviolet ray protection effect, and has a less sense of burden on the skin and good use feeling thereon.

The present inventors have found that the issue can be solved by an oil-in-water type sunscreen cosmetic that contains emulsion particles containing an oil soluble ultraviolet ray absorbent, and prescribed particles containing an oil soluble ultraviolet ray absorbent encompassed by an ionic surfactant and a hydrophobic amphiphilic substance, in the prescribed amounts respectively.

The oil-in-water type sunscreen cosmetic of the present invention can provide a coating film excellent in uniformity and water resistance, can provide an excellent ultraviolet ray protection effect, and has a less sense of burden on the skin and good use feeling thereon.

The mechanism of the aforementioned effects exerted by the sunscreen cosmetic of the present invention can be considered as follows.

The use of an oil soluble ultraviolet ray absorbent as an ultraviolet ray absorbent in an oil-in-water type sunscreen cosmetic provides excellent water resistance. However, in the case where the oil soluble ultraviolet ray absorbent is contained directly in the oil-in-water type sunscreen cosmetic, the oil soluble ultraviolet ray absorbent migrates to the oil phase to decrease the content of the oil soluble ultraviolet ray absorbent in the water phase. In the case where this oil-in-water type sunscreen cosmetic is coated on the skin and dried, the dried coating film has fine gaps occurring in the portions where the water phase of the cosmetic exist, and an ultraviolet ray is transmitted through the gaps to fail to provide a sufficient ultraviolet ray protection effect.

It has been found that the oil-in-water type sunscreen cosmetic of the present invention can provide a coating film after coating and drying that is enhanced in uniformity and water resistance, due to the use of two kinds of particles, i.e., the component (A) or the component (A1) and the component (B), both of which each contain an oil soluble ultraviolet ray absorbent. It has also been found that the sense of burden in coating on the skin can be reduced, and an excellent use feeling can be provided by regulating the contents thereof to the prescribed ranges.

The emulsion particles as the component (A) or the component (A1) are particles containing an oil soluble ultraviolet ray absorbent (a1), have an average particle diameter of more than 6 μm and 300 μm or less, and are considered to exhibit the ultraviolet ray protection effect mainly by existing in the oil phase of the oil-in-water type sunscreen cosmetic. On the other hand, the particles as the component (B) have a structure containing an oil soluble ultraviolet ray absorbent (b3) encompassed by an ionic surfactant (b1) and a hydrophobic amphiphilic substance (b2). The particles have hydrophilicity and thus can be dispersed in the water phase, and also have a mechanical strength, with which the particle shape can be retained on the skin even after evaporating the aqueous medium in the water phase. Furthermore, the component (B) is fine particles having an average particle diameter of 6 μm or less. Accordingly, it is considered that with the use of the component (B) in combination, the gaps derived from the water phase occurring in the dried coating film formed by coating and drying the oil-in-water type sunscreen cosmetic on the skin can be filled with the component (B), resulting in the enhancement of the uniformity and the water resistance of the coating film.

From the standpoint of the achievement of the aforementioned effects, the component (B) is preferably particles having an α-gel structure (α-gel particles) described later.

The component (B) has a content of a solid oil agent of the prescribed amount or less, and thereby the sunscreen cosmetic of the present invention can have a less sense of burden in coating on the skin.

Examples of the form of the oil-in-water type sunscreen cosmetic of the present invention include a skin lotion, a milky lotion, a cream, a gel, and a beauty essence. A sheet type cosmetic may be produced by impregnating or coating a sheet type substrate, such as a woven fabric or a nonwoven fabric, therewith.

The oil-in-water type sunscreen cosmetic of the present invention can be used by coating on the skin, preferably on the skin except for the scalp skin, and more preferably on any of the face, the body, and the limbs.

<Oil-in-Water Type Sunscreen Cosmetic (1)>

The oil-in-water type sunscreen cosmetic (1) of the present invention contains the following component (A) and the following component (B).

(A) 1% by mass or more and 40% by mass or less of emulsion particles containing an oil soluble ultraviolet ray absorbent (a1), having an average particle diameter of more than 6 μm and 300 μm or less (B) 0.3% by mass or more and 2.5% by mass or less of particles containing an oil soluble ultraviolet ray absorbent (b3) encompassed by an ionic surfactant (b1) and a hydrophobic amphiphilic substance (b2), having a content of a solid oil agent of 2.5% by mass or less based on the total amount of the particles, having an average particle diameter of 6 μm or less <Component (A)>

The oil-in-water type sunscreen cosmetic (1) of the present invention contains, as the component (A), emulsion particles containing an oil soluble ultraviolet ray absorbent (a1) having an average particle diameter of more than 6 μm and 300 μm or less.

The sunscreen cosmetic (1) of the present invention can provide the uniformity and the water resistance of the coating film and the good use feeling due to the component (A) contained, through the mechanism described above.

(Oil Soluble Ultraviolet Ray Absorbent (a1))

Examples of the oil soluble ultraviolet ray absorbent (a1) used in the component (A) include a salicylic acid based ultraviolet ray absorbent, a p-aminobenzoic acid based ultraviolet ray absorbent, a cinnamic acid based ultraviolet ray absorbent, a benzophenone based ultraviolet ray absorbent, a triazine based ultraviolet ray absorbent, a benzoylmethane based ultraviolet ray absorbent, and other organic ultraviolet ray absorbents that are oil soluble. In the description herein, the term "oil soluble" means that the solubility in water at 25° C. is 1 w/w % or less.

Specific examples of the oil soluble ultraviolet ray absorbent (a1) include a salicylic acid based ultraviolet ray absorbent, such as homomenthyl salicylate (homosalate, e.g., "Parsol HMS", produced by DSM N.V.) and octyl salicylate (e.g., "Parsol EHS", produced by DSM N.V.);

a p-aminobenzoic acid based ultraviolet ray absorbent, such as p-aminobenzoic acid, ethyldihydroxypropyl-p-aminobenzoic acid, glyceryl-p-aminobenzoic acid, octyldimethyl-p-aminobenzoic acid, amyl p-dimethylaminobenzoate, and 2-ethylhexyl p-dimethylaminobenzoate;

a cinnamic acid based ultraviolet ray absorbent, such as 2-ethylhexyl p-methoxycinnamate (e.g., "Uvinul MC80", produced by BASF SE), glyceryl mono-2-ethylhexanoate di-p-methoxycinnamate, methyl 2,5-diisopropylcinnamate, methylbis(trimethylsiloxy)silylisopentyl trimethoxycinnamate, and a mixture of isopropyl p-methoxycinnamate and diisopropyl cinnamate;

a benzophenone based ultraviolet ray absorbent, such as 4-(2-ß-glucopyranosiloxy)propoxy-2-hydroxybenzophenone, dihydroxydimethoxybenzophenone, sodium dihydroxydimethoxybenzophenonedisulfonate, 2-hydroxy-4-methoxybenzophenone, 2-hydroxy-4-methoxybenzophenone-5-sulfuric acid, 2,2'-dihydroxy-4-methoxybenzophenone, 2,4-dihydroxybenzophenone, 2,2', 4,4'-tetrahydroxybenzophenone, 2,2'-dihydroxy-4,4'-dimethoxybenzophenoen, and 2-hydroxy-4-N-octoxybenzophenoen;

a triazine based ultraviolet ray absorbent, such as 2,4,6-tris(4-(2-ethylhexyloxycarbonyl)anilino)-1,3,5-triazine (which may be hereinafter referred to as "ethylhexyltriazone", e.g., "Uvinul T150", produced by BASF SE) and bis(ethylhexyloxyphenol)methoxyphenyltriazine (e.g., "Tinosorb S", produced by BASF SE);

a benzoylmethane based ultraviolet ray absorbent, such as 2-phenylbenzimidazole-5-sulfuric acid, 4-isopropyldibenzoylmethane, and 4-tert-butyl-4'-methoxydibenzoylmethane (e.g., "Parsol 1789", produced by DSM N.V.);

octocrylene (e.g., "Parsol 340", produced by DSM N.V.), 1-(3,4-dimethoxyphenyl)-4,4-dimethyl-1,3-pentanedione, cinoxate, methyl o-aminobenzoate, and 3-(4-methylbenzylidene)camphor; and 2-ethylhexyl dimethoxybenzylidenedioxoimidazolidinepropionate (e.g., "Soft Shade DH", produced by Ajinomoto Co., Inc.), hexyl diethylaminohydroxybenzoylbenzoate (e.g., "Uvinul Aplus Glanular", produced by BASF SE), and methylenebisbenzotriazolyltetramethylbutylphenol (e.g., "Tinosorb M", produced by BASF SE).

One kind or two or more kinds of these materials may be used. Two or more kinds of the oil soluble ultraviolet ray absorbents are preferably used in combination from the standpoint of the protection against both UV-A and UV-B.

From the standpoint of the ultraviolet ray protection effect, the oil soluble ultraviolet ray absorbent (a1) is preferably one or more kind selected from the group consisting of homomenthyl salicylate, octyl salicylate, 2-ethylhexyl p-methoxycinnamate, ethylhexyltriazone, bis(ethylhexyloxyphenol)methoxyphenyltriazine, 4-tert-butyl-4'-methoxydibenzoylmethane, octocrylene, 2-ethylhexyl dimethoxybenzylidenedioxoimidazolidinepropionate, and hexyl diethylaminohydroxybenzoylbenzoate, more preferably one or more kind selected from the group consisting of 2-ethylhexyl p-methoxycinnamate, ethylhexyltriazone, bis(ethylhexyloxyphenol)methoxyphenyltriazine, and hexyl diethylaminohydroxybenzoylbenzoate, and further preferably the combination use of 2-ethylhexyl p-methoxycinnamate, ethylhexyltriazone, bis(ethylhexyloxyphenol)methoxyphenyltriazine, and hexyl diethylaminohydroxybenzoylbenzoate.

The oil soluble ultraviolet ray absorbent (a1) is also more preferably one or more kind selected from the group consisting of homomenthyl salicylate, octyl salicylate, 4-tert-butyl-4'-methoxydibenzoylmethane, and octocrylene, and further preferably the combination use of homomenthyl salicylate, octyl salicylate, 4-tert-butyl-4'-methoxydibenzoylmethane, and octocrylene.

(Liquid Oil Agent (a2))

The component (A) may further contain a liquid oil agent (a2) other than the component (a1) from the standpoint of the enhancement of the use feeling and the compatibility with the oil soluble ultraviolet ray absorbent (a1). In the description herein, the term "liquid" means the presence of fluidity at 25° C. under ordinary pressure, and the judgement as a liquid is made by the liquid-solid judgement test according to the standard by American Society for Testing and Materials "ASTM D 4359-90, Standard Test Method for Determining Whether a Material Is a Liquid or a Solid".

The liquid oil agent (a2) is not particularly limited, as far as it is a liquid oil agent used in the ordinary cosmetics, and may be any of a synthetic oil and a natural oil.

Examples of the synthetic oil include a linear or branched hydrocarbon oil, such as liquid paraffin, light liquid isoparaffin, squalane, and squalene;

an ester oil, such as a fatty acid monoester formed of a fatty acid and a monohydric alcohol, e.g., cetyl 2-ethylhexanoate, isopropyl myristate, isopropyl palmitate, hexadecyl myristate, 2-octyldodecyl myristate, hexadecyl palmitate, and 2-ethylhexyl stearate, an aromatic carboxylic acid monoester formed of an aromatic carboxylic acid and a monohydric alcohol, e.g., an alkyl benzoate (such as "Finsolv TN", an alkyl (C12-15) benzoate, produced by Innospec Active Chemicals, LLC), and a polyhydric alcohol fatty acid ester formed of a fatty acid and a polyhydric alcohol, e.g., neopentyl glycol dicaprate and pentaerythritol tetra-2-ethylhexanoate;

a silicone oil (preferably except for the methylphenylpolysiloxane described later), such as dimethylpolysiloxane, dimethylcyclopolysiloxane, methylhydrogenpolysiloxane, and a higher alcohol-modified silicone oil; and a fluorine oil, such as a fluoropolyether and a perfluoroalkyl ether silicone.

Examples of the natural oil include a vegetable oil, such as jojoba oil and olive oil; and an animal oil, such as liquid lanolin.

From the stand point of the enhancement of the use feeling and the compatibility with the oil soluble ultraviolet ray absorbent (a1), among these materials, the liquid oil agent (a2) is preferably one or more kind of a synthetic oil selected from the group consisting of a linear or branched hydrocarbon oil, an ester oil, and a silicone oil, more preferably an ester oil, and further preferably one or more kind selected from the group consisting of a fatty acid monoalkyl ester and an aromatic carboxylic acid monoalkyl ester.

The content of the oil soluble ultraviolet ray absorbent (a1) based on the total amount of the oil soluble ultraviolet ray absorbent (a1) and the liquid oil agent (a2) in the component (A) is preferably 60% by mass or more, more preferably 65% by mass or more, and further preferably 70% by mass or more, from the standpoint of the enhancement of the ultraviolet ray protection effect and the reduction of the sense of burden on the skin. The upper limit thereof is 100% by mass, and is preferably 98% by mass or less, and more preferably 95% by mass or less, from the same standpoint as above. The specific range of the content of the oil soluble ultraviolet ray absorbent (a1) based on the total amount of the oil soluble ultraviolet ray absorbent (a1) and the liquid oil agent (a2) in the component (A) is preferably 60 to 100% by mass, more preferably 65 to 98% by mass, and further preferably 70 to 95% by mass.

(Emulsifier)

The component (A) may further contain an emulsifier from the standpoint of the ease of producing and the emulsion stability of the emulsion particles. Examples of the emulsifier include various surfactants, such as a cationic surfactant, an anionic surfactant, a nonionic surfactant, and an amphoteric surfactant. A nonionic surfactant is preferred from the standpoint of the dispersion of the oil soluble ultraviolet ray absorbent (a1) and the emulsion stability.

Examples of the nonionic surfactant include a polyoxyethylene alkyl aryl ether compound or a polyoxyethylene alkyl ether compound, such as polyoxyethylene nonyl phenyl ether, polyoxyethylene oleyl ether, polyoxyethylene lauryl ether, polyoxyethylene 2-hexyldecyl ether, and polyoxyethylene octyl dodecyl ether; a polyoxyethylene fatty acid ester compound, such as polyethylene glycol monolaurate, polyethylene glycol monostearate, and polyethylene glycol monooleate; and an oxyethylene-oxypropylene block copolymer, and one kind or two or more kinds thereof may be used. Among these, a polyoxyethylene alkyl ether compound is preferred from the standpoint of the emulsion stability.

Examples of the commercially available product of the polyoxyethylene alkyl ether compound include "Emulgen" Series, produced by Kao Corporation.

In the case where an emulsifier is used in the component (A), the content thereof is preferably 0.01% by mass or more, more preferably 0.05% by mass or more, and further preferably 0.1% by mass or more, from the standpoint of the dispersion of the oil soluble ultraviolet ray absorbent (a1) and the emulsion stability, and is preferably 5% by mass or less, more preferably 3% by mass or less, and further preferably 1% by mass or less, from the standpoint of the achievement of the use feeling without stickiness, all based on the total amount of the oil soluble ultraviolet ray absorbent (a1) and the liquid oil agent (a2) in the component (A) as 100% by mass. The specific content range of the emulsifier in the component (A) is preferably 0.01 to 5% by mass, more preferably 0.05 to 3% by mass, and further preferably 0.1 to 1% by mass, based on the total amount of the oil soluble ultraviolet ray absorbent (a1) and the liquid oil agent (a2) as 100% by mass.

(Production of Component (A))

The component (A) is preferably produced by the method described in the step (I) described later. Specifically, an emulsion containing emulsion particles (A) may be produced by emulsifying an oil phase containing the oil soluble ultraviolet ray absorbent (a1) in an aqueous medium with an emulsifier. The details thereof will be described later.

(Average Particle Diameter)

The average particle diameter of the emulsion particles as the component (A) is more than 6 μm, preferably 10 μm or more, and more preferably 15 μm or more, from the standpoint of the water resistance and the ease of producing of the coating film. The average particle diameter of the component (A) is 300 μm or less, preferably 200 μm or less, more preferably 100 μm or less, and further preferably 50 μm or less, from the standpoint of the storage stability. The specific range of the average particle diameter of the component (A) is preferably 10 to 200 μm, more preferably 10 to 100 μm, and further preferably 15 to 50 μm.

In the description herein, the average particle diameter means a median diameter (D50). The average particle diameter is a value that is measured at 25° C. with a laser diffraction-scattering particle diameter distribution measuring equipment, and may be measured specifically by the method described in the examples.

(Content of Component (A))

The content of the component (A) in the sunscreen cosmetic (1) of the present invention is 1% by mass or more, preferably 5% by mass or more, more preferably 10% by mass or more, and further preferably 15% by mass or more, from the standpoint of the uniformity and the water resistance of the coating film and the reduction of the sense of burden on the skin. The content of the component (A) is 40% by mass or less, preferably 35% by mass or less, more preferably 30% by mass or less, and further preferably 25% by mass or less, from the same standpoint. The specific range of the content of the component (A) in the sunscreen cosmetic (1) of the present invention is 1 to 40% by mass, preferably 5 to 35% by mass, more preferably 10 to 30% by mass, and further preferably 15 to 25% by mass. The content of the component (A) may be obtained as the total amount of the oil soluble ultraviolet ray absorbent (a1), the liquid oil agent (a2) and the emulsifier.

<Component (B)>

The oil-in-water type sunscreen cosmetic (1) of the present invention contains, as the component (B), particles containing an oil soluble ultraviolet ray absorbent (b3) encompassed by an ionic surfactant (b1) and a hydrophobic amphiphilic substance (b2), having a content of a solid oil agent of 2.5% by mass or less based on the total amount of the particles, having an average particle diameter of 6 μm or less.

The sunscreen cosmetic of the present invention can provide the uniformity and the water resistance of the coating film and the good use feeling due to the component (B) contained, through the mechanism described above.

(Ionic Surfactant (b1))

Examples of the ionic surfactant as the component (b1) include an anionic surfactant, a cationic surfactant, and an amphoteric surfactant. An anionic surfactant is preferred from the standpoint of the achievement of the uniformity of the coating film through the mechanism described above, and the enhancement of the water resistance, the use feeling, and the storage stability.

The anionic surfactant used as the component (b1) preferably contains a long-chain N-acylglutamate salt from the standpoint of obtaining particles having an α-gel structure (α-gel particles) described later, and the long-chain N-acylglutamate salt is preferably at least one kind selected from sodium N-lauroyl-L-glutamate, sodium N-stearoyl-L-glutamate, arginine N-stearoyl-L-glutamate, and sodium N-myristoyl-L-glutamate, more preferably at least one kind selected from sodium N-stearoyl-L-glutamate and arginine N-stearoyl-L-glutamate, and further preferably arginine N-stearoyl-L-glutamate. The ionic surfactant may be used alone or as a combination of two or more kinds thereof.

(Hydrophobic Amphiphilic Substance (b2))

Examples of the hydrophobic amphiphilic substance as the component (b2) include a ceramide compound, an alcohol having 10 or more and 24 or less carbon atoms, a linear saturated fatty acid having 10 or more and 24 or less carbon atoms, a monoglycerin ester of a fatty acid having 10 or more and 24 or less carbon atoms, a monoalkyl glyceryl ether having an alkyl group having 10 or more and 24 or less carbon atoms, a sorbitan ester of a fatty acid having 10 or more and 24 or less carbon atoms, and a monosorbit ester of a fatty acid having 10 or more and 24 or less carbon atoms.

[Ceramide Compound]

The ceramide compound used may be one or more kind selected from the group consisting of a natural ceramide and a pseudo ceramide. The ceramide compound described in JP 2013-53146 is preferred from the standpoint of the enhancement of the stability of the component (B).

Specific examples of the natural ceramide include Ceramide Types 1 to 7 obtained through amidation of sphingosine, dihydrosphingosine, phytosphingosine or sphingadienine (such as the ceramides of swine and human described in FIG. 2 of J. Lipid Res., 24:759 (1983) and FIG. 4 of J. Lipid Res., 35:2069 (1994)). N-alkylated compound (such as N-methylated compounds) thereof are also included.

These ceramides used may be a natural optically active isomer (D(−)-isomer), a non-natural optically active isomer (L(+)-isomer), and a mixture thereof. The relative steric configurations of these compound are not particularly limited. In particular, the compounds of Ceramide 1, Ceramide 2, Ceramide 3, Ceramide 5, and Ceramide 6II (all according to INCI, 8th Edition), and the materials represented by the following formulae are preferred.

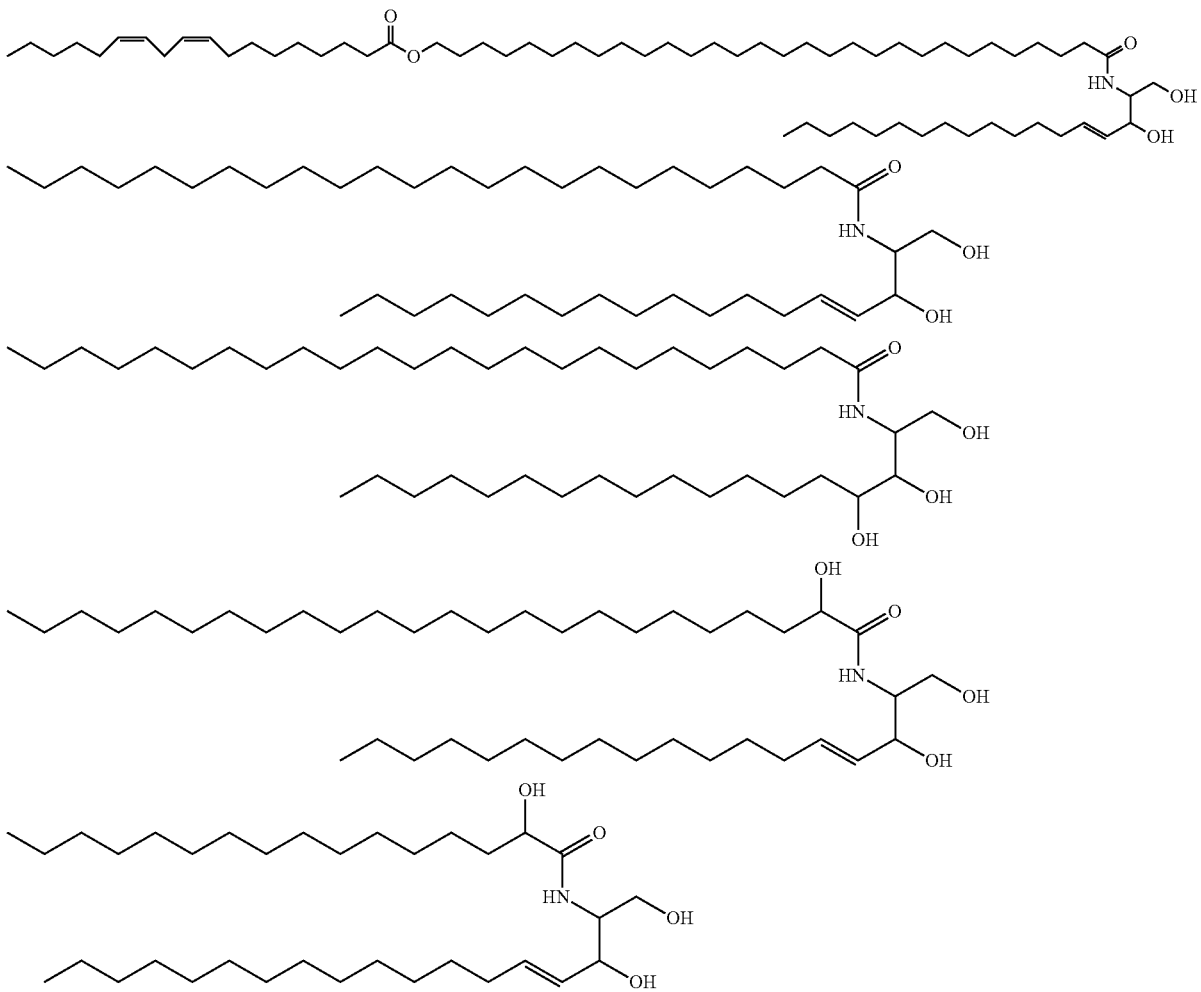

-continued

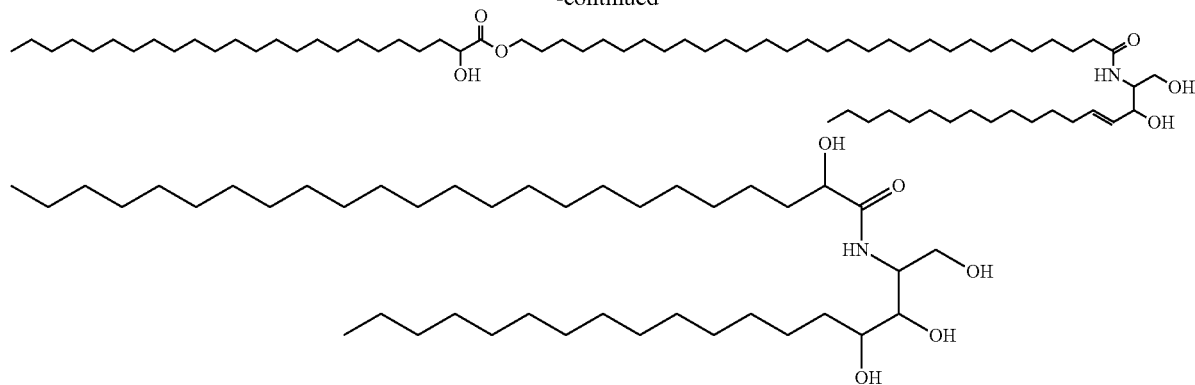

Examples of the commercially available product of the natural ceramide include Ceramide I, Ceramide III, Ceramide IIIA, Ceramide IIIB, Ceramide IIIC, and Ceramide VI (all produced by Cosmoferm BV), Ceramide TIC-001 (produced by Takasago International Corporation), CERAMIDE II (produced by Quest International, Ltd.), DS-Ceramide VI, DS-CLA-Phytoceramide, C6-Phytoceramide, and DS-ceramide Y3S (all produced by Doosan Corporation), and CERAMIDE 2 (produced by Sederma S.A.).

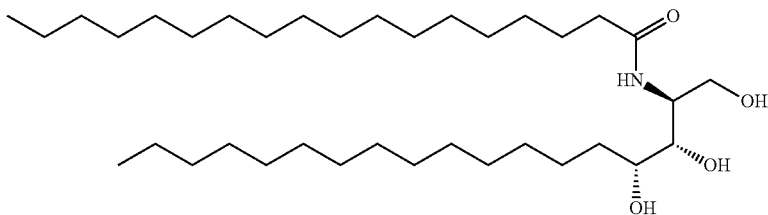

Ceramide III (Cosmoferm BV)

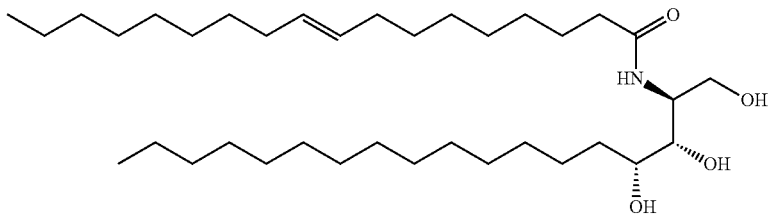

Ceramide III B (Cosmoferm BV)

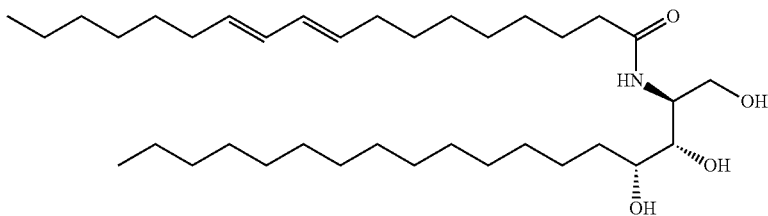

Ceramide III A (Cosmoferm BV)

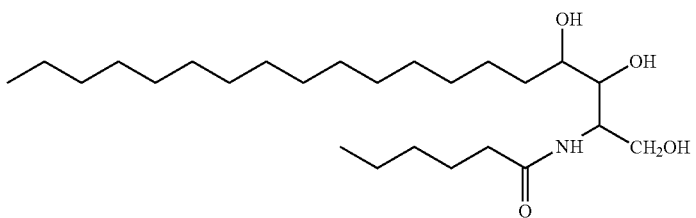

Phytoceramide (Doosan Corporation)

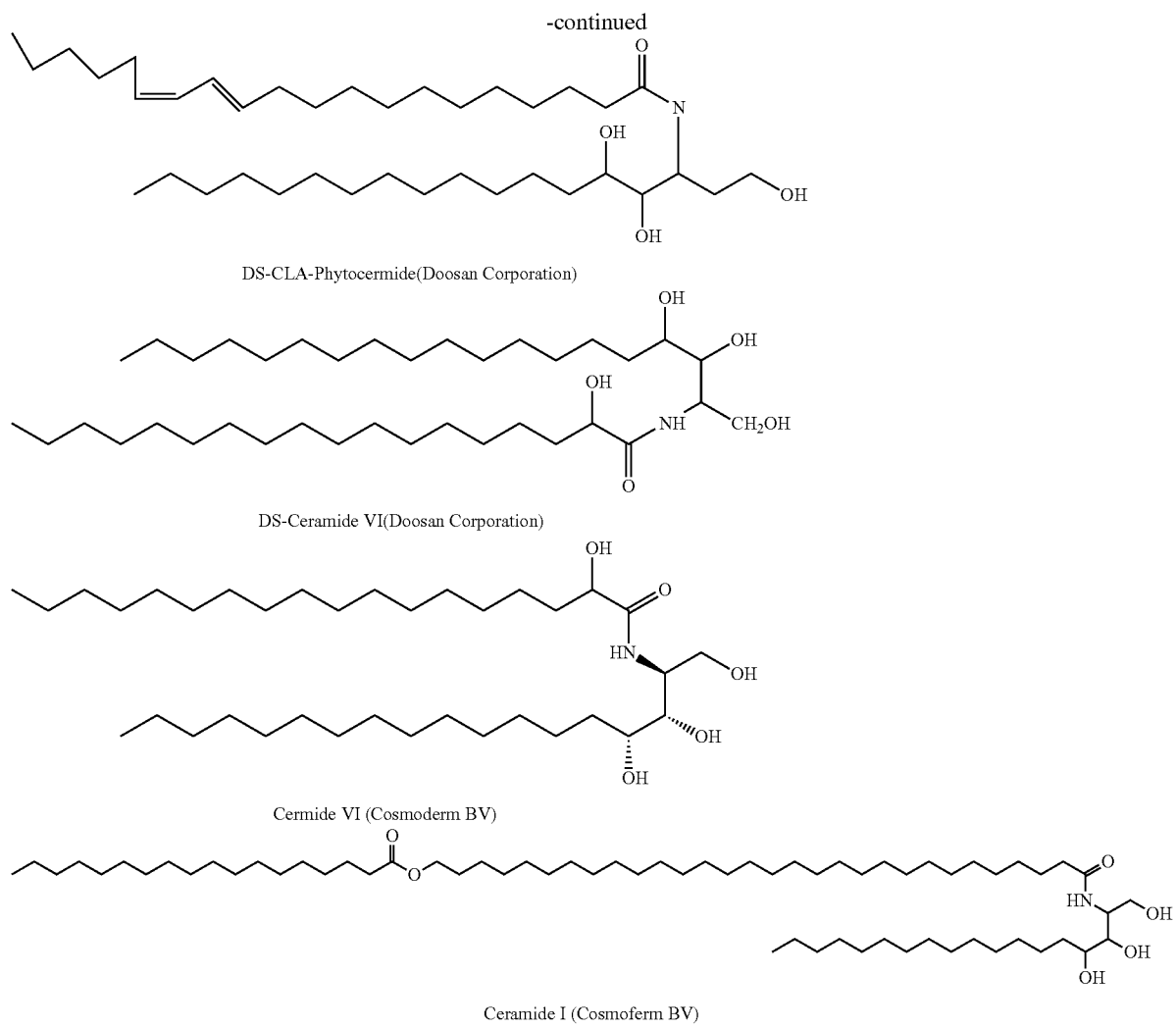

DS-CLA-Phytocermide(Doosan Corporation)

DS-Ceramide VI(Doosan Corporation)

Cermide VI (Cosmoderm BV)

Ceramide I (Cosmoferm BV)

The pseudo ceramide is preferably a pseudo ceramide represented by the following general formula (1) from the standpoint of the enhancement of the stability of the component (B).

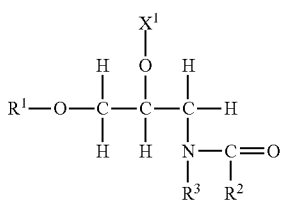

In the formula, $R^1$ represents a linear, branched, or cyclic hydrocarbon group having 10 or more and 22 or less carbon atoms, which may have a hydroxy group, or a hydrogen atom. $X^1$ represents a hydrogen atom, an acetyl group, or a glyceryl group. $R^2$ represents a linear, branched, or cyclic hydrocarbon group having 5 or more and 22 or less carbon atoms, the hydrocarbon group which may have a hydroxy group or an amino group, or to which a linear or branched saturated or unsaturated fatty acid having 8 or more and 22 or less carbon atoms, which may have a hydroxy group is bonded to the w-terminus thereof through an ester bond. $R^3$ represents a hydrogen atom or an alkyl group having a total number of carbon atoms of 1 or more and 30 or less, which may have a hydroxy group, a hydroxyalkoxy group, an alkoxy group, or an acetoxy group.

The pseudo ceramides represented by the following formulae are preferred from the standpoint of the enhancement of the stability of the component (B).

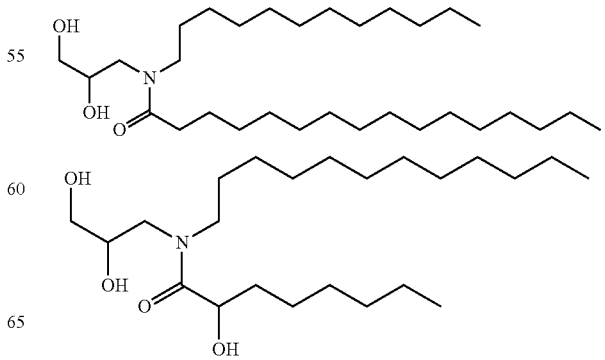

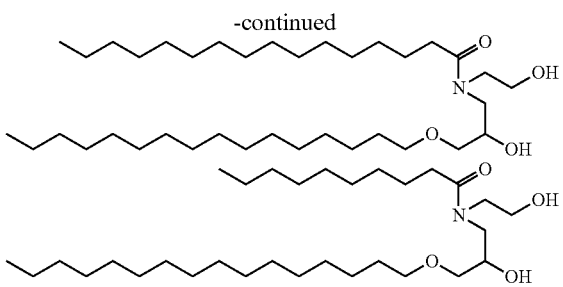

[Alcohol Having 10 or More and 24 or Less Carbon Atoms]

Examples of the alcohol having 10 or more and 24 or less carbon atoms include the alcohol having a linear or branched alkyl or alkenyl group having 10 or more and 24 or less carbon atoms, and the number of carbon atoms thereof is preferably 12 or more and 24 or less, more preferably 14 or more and 22 or less, and further preferably 16 or more and 18 or less, from the standpoint of the enhancement of the emulsion stability of the component (B). Examples of the alcohol include lauryl alcohol, myristyl alcohol, cetyl alcohol, stearyl alcohol, behenyl alcohol, and oleyl alcohol. Among these, the alcohol having a linear alkyl group is preferred, one or more kind selected from the group consisting of cetyl alcohol and stearyl alcohol is more preferred, and cetyl alcohol is further preferred.

[Linear Saturated Fatty Acid Having 10 or More and 24 or Less Carbon Atoms]

Examples of the linear saturated fatty acid having 10 or more and 24 or less carbon atoms include lauric acid, myristic acid, palmitic acid, stearic acid, and behenic acid. Among these, from the standpoint of the enhancement of the emulsion stability of the component (B), the number of carbon atoms of the linear saturated fatty acid is preferably 12 or more and 24 or less, more preferably 14 or more and 22 or less, still further preferably 16 or more and 18 or less, and one or more kind selected from the group consisting of palmitic acid and stearic acid is preferred.

[Monoglycerin Ester of Fatty Acid Having 10 or More and 24 or Less Carbon Atoms]

The monoglycerin ester of a fatty acid having 10 or more and 24 or less carbon atoms means a monoester of a fatty acid having 10 or more and 24 or less carbon atoms and glycerin, the number of carbon atoms of the fatty acid is preferably 12 or more and 24 or less, more preferably 14 or more and 22 or less, and further preferably 16 or more and 22 or less, from the standpoint of the enhancement of the emulsion stability of the component (B). Examples of the monoglycerin ester include glycerin monolaurate, glycerin monomyristate, glycerin monopalmitate, glycerin monostearate, glycerin monobehenate, glycerin monooleate, and glycerin monoisostearate. Among these, one or more kind selected from the group consisting of glycerin monopalmitate, glycerin monostearate, and glycerin monobehenate is preferred, and glycerin monobehenate is more preferred.

[Monoalkyl Glyceryl Ether Having Alkyl Group Having 10 or More and 24 or Less Carbon Atoms]

Examples of the monoalkyl glyceryl ether having an alkyl group having 10 or more and 24 or less carbon atoms include monodecyl glyceryl ether, monolauryl glyceryl ether, monomyristyl glyceryl ether, monocetyl glyceryl ether, monostearyl glyceryl ether, and monobehenyl glyceryl ether. The number of carbon atoms of the alkyl is preferably 12 or more and 24 or less, more preferably 14 or more and 22 or less, and further preferably 16 or more and 22 or less, from the standpoint of the enhancement of the emulsion stability of the component (B), and one or more kind selected from the group consisting of monocetyl glyceryl ether, monostearyl glyceryl ether, and monobehenyl glyceryl ether is preferred.

(Sorbitan Ester of Fatty Acid Having 10 or More and 24 or Less Carbon Atoms)

The sorbitan ester of a fatty acid having 10 or more and 24 or less carbon atoms means an ester of a fatty acid having 10 or more and 24 or less carbon atoms and sorbitan, and from the standpoint of the enhancement of the emulsion stability of the component (B), a monoester or a diester of a fatty acid is preferred, and a diester thereof is more preferred. The fatty acid having 10 or more and 24 or less carbon atoms is preferably a linear saturated fatty acid, and examples thereof include lauric acid, myristic acid, palmitic acid, stearic acid, and behenic acid. The number of carbon atoms of the fatty acid is preferably 12 or more and 24 or less, more preferably 14 or more and 22 or less, and further preferably 16 or more and 18 or less, from the standpoint of the enhancement of the emulsion stability of the component (B).

Examples of the sorbitan ester of a fatty acid having 10 or more and 24 or less carbon atoms include a monoester, such as sorbitan monolaurate, sorbitan monomyristate, sorbitan monopalmitate, sorbitan monostearate, and sorbitan monobehenate; and a diester, such as sorbitan dilaurate, sorbitan dimyristate, sorbitan dipalmitate, sorbitan distearate, and sorbitan dibehenate. Among these, one or more kind selected from the group consisting of sorbitan monomyristate, sorbitan monopalmitate, sorbitan monostearate, sorbitan monobehenate, sorbitan dimyristate, sorbitan dipalmitate, sorbitan distearate, and sorbitan dibehenate is preferred, one or more kind selected from the group consisting of sorbitan dimyristate, sorbitan dipalmitate, sorbitan distearate, and sorbitan dibehenate is more preferred, and one or more kind selected from the group consisting of sorbitan dipalmitate and sorbitan distearate is further preferred.

[Monosorbit Ester of Fatty Acid Having 10 or More and 24 or Less Carbon Atoms]

The monosorbit ester of a fatty acid having 10 or more and 24 or less carbon atoms means a monoester of a fatty acid having 10 or more and 24 or less carbon atoms and sorbitol. The fatty acid having 10 or more and 24 or less carbon atoms is preferably a linear saturated fatty acid, and examples thereof include lauric acid, myristic acid, palmitic acid, stearic acid, and behenic acid. The number of carbon atoms of the fatty acid is preferably 12 or more and 24 or less, more preferably 14 or more and 22 or less, and further preferably 16 or more and 18 or less, from the standpoint of the enhancement of the emulsion stability of the component (B).

The component (b2) preferably contains one or more kind selected from the group consisting of an alcohol having 14 or more and 22 or less carbon atoms, a linear saturated fatty acid having 14 or more and 22 or less carbon atoms, a monoglycerin ester of a fatty acid having 14 or more and 22 or less carbon atoms, and a sorbitan ester of a fatty acid having 14 or more and 22 or less carbon atoms, from the standpoint of the enhancement of the storage stability and the ultraviolet ray protection effect, more preferably contains an alcohol having 14 or more and 22 or less carbon atoms, a monoglycerin ester of a fatty acid having 14 or more and 22 or less carbon atoms, and a sorbitan ester of a fatty acid having 14 or more and 22 or less carbon atoms, or more preferably contains an alcohol having 14 or more and 22 or less carbon atoms and a linear saturated fatty acid having 14 or more and 22 or less carbon atoms, and further preferably contains cetyl alcohol, glycerin monobehenate, and sorbitan distearate, or further preferably contains behenyl alcohol and behenic acid, from the standpoint of the obtaining the α-gel particles described later, and the component (b2) is still further preferably cetyl alcohol, glycerin monobehenate, and sorbitan distearate, or is still further preferably behenyl alcohol and behenic acid.

(Oil Soluble Ultraviolet Ray Absorbent (b3))

The oil soluble ultraviolet ray absorbent used as the component (b3) may be one kind or two or more kinds that are the same as the examples described for the oil soluble ultraviolet ray absorbent (a1). The preferred embodiment thereof is the same as those described for the component (a1). The kind of the oil soluble ultraviolet ray absorbent used as the component (b3), the combination thereof in the case where two or more kinds thereof are used, and the content ratio thereof may be the same as or different from the component (a1).

(Encompassment)

For the component (B), for example, an emulsion containing the particles as the component (B) containing the component (b3) encompassed by the components (b1) and (b2) can be obtained by dispersing the components (b1) to (b3) in an aqueous medium, which may be mixed in the sunscreen cosmetic of the present invention.

The content ratios of the components (b1), (b2), and (b3) in the component (B) in terms of mass ratio [(b3)/{(b1)+(b2)}] is preferably 1 or more, and more preferably 2 or more, and is preferably 10 or less, and more preferably 5 or less, from the standpoint of the emulsion stability of the particles as the component (B).

In the description herein, in the case where the component (b1) is an anionic surfactant that is a salt of an acid compound, the content of the component (b1) means the content in terms of acid. For example, in the case where the component (b1) is a long-chain N-acylglutamate salt, the content of the component (b1) means the content of the long-chain N-acylglutamic acid.

(Liquid Oil Agent (b4))

The component (B) may further contain a liquid oil agent (b4) other than the components (b2) and (b3) from the standpoint of the enhancement of the use feeling and the improvement of the compatibility of the components (b1) to (b3).

The liquid oil agent used as the component (b4) may be one kind or two or more kinds that are the same as the examples described for the liquid oil agent (a2). The preferred embodiment thereof is the same as those described for the component (a2). The kind of the liquid oil agent used as the component (b4), the combination thereof in the case where two or more kinds thereof are used, and the content ratio thereof may be the same as or different from the component (a2).

One or more kind of a synthetic oil selected from the group consisting of a linear or branched hydrocarbon oil, an ester oil, and a silicone oil is preferred from the standpoint of the enhancement of the use feeling and the compatibility with the components (b1) to (b3). An ester oil is more preferred, an aromatic carboxylic acid monoester is further preferred, and an alkyl benzoate is still further preferred.

The content of the ionic surfactant (b1) in the component (B) is preferably 0.5% by mass or more, more preferably 1.5% by mass or more, and further preferably 2% by mass or more, from the standpoint of the enhancement of the emulsion stability of the component (B). The content thereof is preferably 10% by mass or less, more preferably 7.5% by mass or less, and further preferably 5% by mass or less, from the same standpoint. The specific range of the content of the ionic surfactant (b1) in the component (B) is preferably 0.5 to 10% by mass, more preferably 1.5 to 7.5% by mass, and further preferably 2 to 5% by mass. The content in the component (B) herein means the content based on the total amount of the ionic surfactant (b1), the hydrophobic amphiphilic substance (b2), the oil soluble ultraviolet ray absorbent (b3), the liquid oil agent (b4), and the solid oil agent described later.

The content of the hydrophobic amphiphilic substance (b2) in the component (B) is preferably 5% by mass or more, more preferably 7.5% by mass or more, and further preferably 10% by mass or more, from the standpoint of the enhancement of the stability of the component (B). The content thereof is preferably 50% by mass or less, more preferably 35% by mass or less, and further preferably 25% by mass or less, from the same standpoint. The specific range of the content of the hydrophobic amphiphilic substance (b2) in the component (B) is preferably 5 to 50% by mass, more preferably 7.5 to 35% by mass, and further preferably 10 to 25% by mass.

The content of the oil soluble ultraviolet ray absorbent (b3) in the component (B) is preferably 30% by mass or more, more preferably 40% by mass or more, and further preferably 50% by mass or more, from the standpoint of the enhancement of the ultraviolet ray protection effect and the enhancement of the stability of the component (B). The content thereof is preferably 95% by mass or less, more preferably 90% by mass or less, and further preferably 85% by mass or less, from the same standpoint. The specific range of the content of the oil soluble ultraviolet ray absorbent (b3) in the component (B) is preferably 30 to 95% by mass, more preferably 40 to 90% by mass, and further preferably 50 to 85% by mass.

In the case where the liquid oil agent (b4) is used, the content of the liquid oil agent (b4) in the component (B) is preferably 1% by mass or more, more preferably 5% by mass or more, and further preferably 10% by mass or more, and is preferably 30% by mass or less, more preferably 25% by mass or less, and further preferably 20% by mass or less, from the standpoint of the enhancement of the use feeling and the compatibility with the components (b1) to (b3). The specific range of the content of the liquid oil agent (b4) in the component (B) is preferably 1 to 30% by mass, more preferably 5 to 25% by mass, and further preferably 10 to 20% by mass.

In the component (B), the content of the solid oil agent with respect to the component (B) is 2.5% by mass or less, preferably 1% by mass or less, more preferably 0.1% by mass or less, and further preferably substantially 0% by mass, from the standpoint of the achievement of a less sense of burden on the skin and good use feeling.

In the description herein, the term "solid" means the absence of fluidity at 25° C. under ordinary pressure, and the judgement as a solid is made by the liquid-solid judgement test according to the standard by American Society for Testing and Materials "ASTM D 4359-90, Standard Test Method for Determining Whether a Material is a Liquid or a Solid".

The solid oil agent does not include the hydrophobic amphiphilic substance (b2) and the oil soluble ultraviolet ray absorbent (b3), and examples thereof include vegetable wax, such as candelilla wax, rice wax, sunflower wax, carnauba wax, and Japan wax; animal wax, such as bees wax and spermaceti wax; mineral wax, such as montan wax and ozokerite; petroleum wax, such as microcrystalline wax, paraffin, and ceresin; and synthetic wax, such as a hardened castor oil, a hydrogenated jojoba oil, 12-hydroxystearic acid, stearic acid amide, silicone wax, and polyethylene wax.

The component (B) is preferably particles having an α-gel structure (α-gel particles). The α-gel particles have excellent robustness, and thus can provide an oil-in-water type sunscreen cosmetic excellent in uniformity and water resistance of the coating film through the mechanism described above. The fact that the particles as the component (B) have an α-gel structure can be confirmed by X-ray diffraction (XRD). Specifically, particles exhibiting at least one sharp peak around a Bragg angle of 21 to 220 in the wide angle X-ray diffraction can be judged as having an α-gel structure.

(Production of Component (B))

The component (B) can be produced by an ordinary emulsification method for cosmetics, and can also be produced by such methods as ultrasonic emulsification, high pressure emulsification, or the like. The component (B) is preferably produced by the method described for the step (II) described later from the standpoint of the obtaining the particles having an α-gel structure. Specifically, the ionic surfactant (b1), the hydrophobic amphiphilic substance (b2), the oil soluble ultraviolet ray absorbent (b3), and the aqueous medium are mixed under heating for emulsifying, and then cooled at a cooling rate of 0.5° C./sec or more and 10° C./sec or less, so as to provide an emulsion containing the particles (B) having an average particle diameter of 6 μm or less, containing the component (b3) encompassed in the components (b1) and (b2). The production method will be described in detail later.

(Average Particle Diameter)

The average particle diameter of the particles as the component (B) is 6 μm or less, preferably 3 μm or less, more preferably 1 μm or less, and further preferably 0.3 μm or less, from the standpoint of the uniformity of the coating film. The average particle diameter of the component (B) is preferably 0.05 μm or more, more preferably 0.08 μm or more, and further preferably 0.1 μm or more, from the standpoint of the ease of producing. The specific range of the average particle diameter of the component (B) is preferably 0.05 to 6 μm, more preferably 0.08 to 3 μm, further preferably 0.1 to 1 μm, and still further preferably 0.1 to 0.3 μm.

(Content of Component (B))

The content of the component (B) in the sunscreen cosmetic (1) of the present invention is 0.3% by mass or more, preferably 0.5% by mass or more, and more preferably 0.7% by mass or more, from the standpoint of the uniformity and the water resistance of the coating film, and is 2.5% by mass or less, preferably 2% by mass or less, more preferably 1.5% by mass or less, and further preferably 1.2% by mass or less, from the standpoint of the uniformity of the coating film and the less sense of burden on the skin. The specific range of the content of the component (B) in the sunscreen cosmetic (1) is 0.3 to 2.5% by mass, preferably 0.5 to 2% by mass, more preferably 0.7 to 1.5% by mass, and further preferably 0.7 to 1.2% by mass.

The content ratio of the component (A) and the component (B) in the sunscreen cosmetic (1) of the present invention in terms of mass ratio (A)/(B) is preferably 5 or more, more preferably 10 or more, and further preferably 15 or more, from the standpoint of the uniformity and the water resistance of the coating film, and is preferably 50 or less, more preferably 40 or less, and further preferably 30 or less, from the same standpoint. The specific range of the mass ratio (A)/(B) is preferably 5 to 50, more preferably 10 to 40, and further preferably 15 to 30.

(Water Soluble Polymer)

The sunscreen cosmetic (1) of the present invention may further contain a water soluble polymer from the standpoint of the enhancement of the storage stability. The water soluble polymer is not particularly limited, as far as it is a polymer that is used in the ordinary cosmetics, and may be any of a natural polymer, a semisynthetic polymer, and a synthetic polymer.

Examples of the natural polymer include xanthane gum, carrageenan, and alginic acid. Examples of the semisynthetic polymer include a modified polysaccharide, such as hydroxycellulose, hydroxypropylcellulose, sodium carboxymethylcellulose, methylcellulose, hydroxymethylcellulose, and cationized cellulose. Examples of the synthetic polymer include an acrylic polymer, such as Carbomer (crosslinked polyacrylic acid), polyacrylic acid, sodium polyacrylate, an alkyl acrylate-methacrylate copolymer, polyacrylamide, a (sodium acrylate-sodium acryloyldimethyltaurine) copolymer, a (hydroxyethyl acrylate-sodium acryloyldimethyltaurine) copolymer, an (acrylamide-ammonium acrylate) copolymer, and an acrylic acid based polymer, e.g., polyacrylate-13; polyvinylpyrrolidone, polyvinyl alcohol, and cationized polyvinylpyrrolidone.

Among these, an acrylic polymer is preferred, one or more kind selected from the group consisting of Carbomer, an alkyl acrylate-methacrylate copolymer, polyacrylamide, a (sodium acrylate-sodium acryloyldimethyltaurine) copolymer, a (hydroxyethyl acrylate-sodium acryloyldimethyltaurine) copolymer, an (acrylamide-ammonium acrylate) copolymer, and polyacrylate-13 is more preferred, and an alkyl acrylate-methacrylate copolymer is further preferred, from the standpoint of the achievement of the good storage stability.

Examples of the commercially available product of the Carbomer include "Carbopol 910", "Carbopol 934", "Carbopol 940", "Carbopol 941", "Carbopol 980", and "Carbopol 981", produced by Lubrizol Advanced Materials, Inc.

Examples of the commercially available product of the alkyl acrylate-methacrylate copolymer include "Carbopol 1382", "Carbopol ETD2020", "Pemulen TR-1", and "Pemulen TR-2", produced by Lubrizol Advanced Materials, Inc.

Examples of the commercially available product of the polyacrylamide include "Sepigel 305", produced by Seppic S.A., and examples of the commercially available product of the (sodium acrylate-sodium acryloyldimethyltaurine) copolymer include "Simulgel EG", produced by Seppic S.A. Examples of the commercially available product of the (hydroxyethyl acrylate-sodium acryloyldimethyltaurine) copolymer include "Simulgel FL", "Simulgel NS", "Sepiplus S", and "Sepinov EMT 10", produced by Seppic S.A.

In the case where the water soluble polymer is used, the content thereof in the sunscreen cosmetic (1) is preferably 0.01% by mass or more, more preferably 0.05% by mass or more, and further preferably 0.1% by mass or more, from the standpoint of the enhancement of the storage stability, and is preferably 5% by mass or less, more preferably 3% by mass or less, and further preferably 1% by mass or less, from the standpoint of the retention of the use feeling. The specific range of the content of the water soluble polymer in the sunscreen cosmetic is preferably 0.01 to 5% by mass, more preferably 0.05 to 3% by mass, and further preferably 0.1 to 1% by mass.

(Aqueous Medium)

The sunscreen cosmetic (1) of the present invention contains at least water as an aqueous medium. In addition, a lower alcohol, such as ethanol and isopropyl alcohol; a low molecular weight diol or triol having 6 or less carbon atoms, such as 1,3-butylene glycol, glycerin, ethylene glycol, and propylene glycol; and the like may be contained depending on necessity.

The content of the aqueous medium in the sunscreen cosmetic (1) may be in such a range that provides an oil-in-water type cosmetic, and is generally 98.7% by mass or less. The content of the aqueous medium in the sunscreen cosmetic may be the balance of the sunscreen cosmetic except for all the active ingredients.

<Other Components>

The sunscreen cosmetic (1) of the present invention may appropriately contain, in addition to the components described above, a beauty component, a medical component, and a component that is ordinarily used in skin cosmetics, in such a range that does not impair the object of the present invention. Examples of the component include a thickener, a sterilizer, a moisturizer, a humectant, a colorant, an antiseptic, a feel improver, a powder material, a fragrance, an anti-inflammatory agent, a whitener, an antiperspirant, an antioxidant, and a pH modifier.

[Production Method of Oil-in-Water Type Sunscreen Cosmetic (1)]

The production method of the oil-in-water type sunscreen cosmetic (1) of the present invention preferably includes the following steps (I) to (III). According to the method, the oil-in-water type sunscreen cosmetic that exerts the effects of the present invention can be efficiently produced.

Step (I): emulsifying an oil phase containing the oil soluble ultraviolet ray absorbent (a1) in an aqueous medium with an emulsifier, so as to provide an emulsion containing the emulsion particles (A) having an average particle diameter of more than 6 μm and 300 μm or less Step (II): mixing the ionic surfactant (b1), the hydrophobic amphiphilic substance (b2), the oil soluble ultraviolet ray absorbent (b3), and an aqueous medium under heating for emulsifying, and then cooling at a cooling rate of 0.5° C./sec or more and 10° C./sec or less, so as to provide an emulsion containing the particles (B) containing the component (b3) encompassed by the components (b1) and (b2), having an average particle diameter of 6 μm or less Step (III): mixing the emulsion containing the emulsion particles (A) obtained in the step (I) and the emulsion containing the particles (B) obtained in the step (II).

(Step (I))

In the step (I), an oil phase containing an oil soluble ultraviolet ray absorbent (a1) is emulsified in an aqueous medium with an emulsifier, so as to provide an emulsion containing emulsion particles (A) having an average particle diameter of more than 6 μm and 300 μm or less.

The emulsifier and the aqueous medium used may be those described above, and the aqueous medium is preferably water. The oil phase may further contain the liquid oil agent (a2).

In the step (I), the component (a1), the emulsifier, the aqueous medium, and the component (a2) and the other components used depending on necessity may be blended and mixed to provide an emulsion containing the emulsion particles as the component (A). Examples of the apparatus used for the emulsification in the step (I) include a homomixer, an ultrasonic emulsification equipment, and a high pressure emulsification equipment.

The mixing temperature may vary depending on the kind of the aqueous medium and the like, and is preferably 60° C. or more, and more preferably 70° C. or more, from the standpoint of the dispersibility, and is preferably 100° C. or less, and more preferably 90° C. or less, from the standpoint of the productivity and the suppression of decomposition of the mixed components.

The amount of the emulsifier used in the step (I), based on the total amount of the oil soluble ultraviolet ray absorbent (a1) and the liquid oil agent (a2) in the component (A) as 100% by mass, may be in the aforementioned range. The amount of the emulsifier in the emulsion in the step (I) is preferably 0.001% by mass or more, more preferably 0.005% by mass or more, and further preferably 0.01% by mass or more, from the standpoint of the emulsion stability, and is preferably 5% by mass or less, more preferably 1% by mass or less, further preferably 0.5% by mass or less, and still further preferably 0.2% by mass or less, from the standpoint of the use feeling (absence of stickiness).

The content of the component (A) in the emulsion obtained in the step (I) is preferably 1% by mass or more, more preferably 5% by mass or more, further preferably 10% by mass or more, and still further preferably 15% by mass or more, from the standpoint of the easiness in controlling the mixing ratio, and is preferably 40% by mass or less, more preferably 35% by mass or less, further preferably 32% by mass or less, and still further preferably 25% by mass or less, from the standpoint of the ease of producing. The content of the component (A) in the emulsion obtained in the step (I) means the total amount of the oil soluble ultraviolet ray absorbent (a1), the liquid oil agent (a2), and the emulsifier.

(Step (II))

In the step (II), the ionic surfactant (b1), the hydrophobic amphiphilic substance (b2), the oil soluble ultraviolet ray absorbent (b3), and an aqueous medium are mixed under heating for emulsifying, and then cooled at a cooling rate of 0.5° C./sec or more and 10° C./sec or less, so as to provide an emulsion containing the particles (B) containing the component (b3) encompassed by the components (b1) and (b2), having an average particle diameter of 6 μm or less.

In the step (II), the components (b1) to (b3), the aqueous medium, and the other components used depending on necessity can be emulsified by blending and mixing under heating (emulsifying step).

The mixing temperature under heating may vary depending on the kind of the aqueous medium and the like, and is preferably 60° C. or more, and more preferably 70° C. or more, from the standpoint of the dispersibility and the control of the particle diameter of the particles (B), and is preferably 120° C. or less, and more preferably 100° C. or less, from the standpoint of the productivity and the suppression of decomposition of the mixed components.

Examples of the apparatus used in the emulsifying step in the step (II) include a homomixer, an ultrasonic emulsification equipment, and a high pressure emulsification equipment. Among these, a high pressure emulsification equipment is preferably used from the standpoint of the control of the particle diameter of the particles (B). This is because the average particle diameter of the particles (B) can be readily controlled to the target range by controlling the pressure condition. The pressurization condition in the case where a high pressure emulsification equipment is used may be set, for example, to a range of ordinary pressure (0 MPa) to 100 MPa.

Subsequently, the liquid obtained after the emulsifying step is cooled at a cooling rate of 0.5° C./sec or more and 10° C./sec or less (cooling step), so as to provide an emulsion containing the particles (B). According to the operation, the particles (B) having an α-gel structure can be formed.

The cooling rate is preferably 0.5° C./sec or more, and more preferably 0.8° C./sec or more, from the standpoint of the formation of an α-gel structure. The cooling rate is preferably 10° C./sec or less, and more preferably 8° C./sec or less, from the standpoint of the stable formation of particles. The specific range of the cooling rate is preferably 0.5 to 10° C./sec, and more preferably 0.8 to 8° C./sec.

In the cooling step in the step (II), a method of rapidly cooling continuously with a vibration agitation mixing equipment, a scraping heat exchanger (Onlator, produced by Sakura Seisakusho, Ltd.), Static Mixer (produced by Noritake Co., Ltd.), an ordinary plate type heat exchanger, an ordinary double pipe heat exchanger, or the like, and a method of cooling under agitation in an ordinary mixing tank may be used. Among these, the method using a vibration agitation mixing equipment is preferred. The vibration agitation mixing equipment has an agitation body including a driving axle and an agitation blade attached to the driving axle in a tubular casing, in which the driving axle is vibrated in the axial direction, and the agitation blade preferably has one or more opening and/or one or more notch formed therein.

In the cooling step, it is preferred that the liquid obtained in the emulsifying step is fed into the vibration agitation mixing equipment, and continuously cooling under agitation through the vibration of the agitation blade, and thereby an emulsion having the fine particles (B) having an α-gel structure dispersed in the aqueous medium can be obtained.

Examples of the ultrasonic emulsification equipment or the high pressure emulsification equipment used in the emulsifying step of the step (II) and the vibration agitation mixing equipment used in the cooling step thereof include those described in JP 2017-7969 A.

The content of the component (B) in the emulsion obtained in the step (II) is preferably 5% by mass or more, and more preferably 10% by mass or more, from the standpoint of the easiness in controlling the mixing ratio, and is preferably 30% by mass or less, and more preferably 20% by mass or less, from the standpoint of the ease of producing. The content of the component (B) in the emulsion obtained in the step (II) means the total amount of the ionic surfactant (b1), the hydrophobic amphiphilic substance (b2), the oil soluble ultraviolet ray absorbent (b3), the liquid oil agent (b4), and the solid oil agent.

(Step (III))

In the step (III), the emulsion containing the emulsion particles (A) obtained in the step (I) and the emulsion containing the particles (B) obtained in the step (II) are mixed in such amounts that provide the contents of the component (A) and the component (B) within the target ranges. In the case where the water soluble polymer described above is used, the water soluble polymer is preferably mixed in the step (III). In the step (III), the pH may be controlled by mixing a pH modifier, such as an alkali agent.

The mixing in the step (III) may be performed with a known agitation equipment. The mixing temperature is generally in a range of 5° C. or more and 50° C. or less from the standpoint of the productivity.

<Oil-in-Water Type Sunscreen Cosmetic (2)>

The oil-in-water type sunscreen cosmetic (2) of the present invention contains the following component (A1) and the following component (B).

(A1) 1% by mass or more and 40% by mass or less of emulsion particles containing an oil soluble ultraviolet ray absorbent (a1) and a methylphenylpolysiloxane (a3), having an average particle diameter of more than 6 μm and 300 μm or less (B) 0.3% by mass or more and 5% by mass or less of particles containing an oil soluble ultraviolet ray absorbent (b3) encompassed by an ionic surfactant (b1) and a hydrophobic amphiphilic substance (b2), having a content of a solid oil agent of 2.5% by mass or less based on the total amount of the particles, having an average particle diameter of 6 μm or less <Component (A1)>

The oil-in-water type sunscreen cosmetic (2) of the present invention contains, as the component (A1), emulsion particles containing an oil soluble ultraviolet ray absorbent (a1) and a methylphenylpolysiloxane (a3), having an average particle diameter of more than 6 μm and 300 μm or less.

The sunscreen cosmetic (2) of the present invention can provide the uniformity and the water resistance of the coating film and the good use feeling due to the component (A1) contained, through the mechanism described above. The sunscreen cosmetic (2) can also reduce the sense of burden on the skin, and the content of the component (B) can be increased to an upper limit of 5% by mass beyond 2.5% by mass, due to the methylphenylpolysiloxane (a3) contained in the component (A1).

Examples of the methylphenylpolysiloxane (a3) include phenyl trimethicone and the like.

The content of the oil soluble ultraviolet ray absorbent (a1) based on the total amount of the oil soluble ultraviolet ray absorbent (a1) and the methylphenylpolysiloxane (a3) in the component (A1) is preferably 60% by mass or more, more preferably 65% by mass or more, and further preferably 70% by mass or more, from the standpoint of the enhancement of the ultraviolet ray protection effect and the reduction of the sense of burden on the skin. The upper limit thereof is less than 100% by mass, and is preferably 98% by mass or less, and more preferably 95% by mass or less, from the same standpoint as above. The specific range of the content of the oil soluble ultraviolet ray absorbent (a1) based on the total amount of the oil soluble ultraviolet ray absorbent (a1) and the methylphenylpolysiloxane (a3) in the component (A1) is preferably 60% by mass or more and less than 100% by mass, more preferably 60 to 98% by mass, further preferably 65 to 98% by mass, and still further preferably 70 to 95% by mass.

(Emulsifier)

The component (A1) may further contain an emulsifier from the standpoint of the ease of producing and the emulsion stability of the emulsion particles. The emulsifier used may be the same ones as exemplified for the oil-in-water type sunscreen cosmetic (1).

In the case where an emulsifier is used in the component (A1), the content thereof is preferably 0.01% by mass or more, more preferably 0.05% by mass or more, and further preferably 0.1% by mass or more, from the standpoint of the dispersion of the oil soluble ultraviolet ray absorbent (a1) and the emulsion stability, and is preferably 5% by mass or less, more preferably 3% by mass or less, and further preferably 1% by mass or less, from the standpoint of the achievement of the use feeling without stickiness, all based on the total amount of the oil soluble ultraviolet ray absorbent (a1) and the methylphenylpolysiloxane (a3) in the component (A1) as 100% by mass. The specific content range of the emulsifier in the component (A) is preferably 0.01 to 5% by mass, more preferably 0.05 to 3% by mass, and further preferably 0.1 to 1% by mass, based on the total amount of the oil soluble ultraviolet ray absorbent (a1) and the methylphenylpolysiloxane (a3) as 100% by mass.

The production method, the average particle diameter and the preferred ranges thereof of the component (A1) are the same as in the component (A) in the oil-in-water type sunscreen cosmetic (1).

(Content of Component (A1))

The content of the component (A1) in the sunscreen cosmetic (2) of the present invention is 1% by mass or more, preferably 5% by mass or more, more preferably 10% by mass or more, and further preferably 15% by mass or more, from the standpoint of the uniformity and the water resistance of the coating film and the reduction of the sense of burden on the skin. The content of the component (A1) is 40% by mass or less, preferably 35% by mass or less, more preferably 30% by mass or less, and further preferably 25% by mass or less, from the same standpoint. The specific range of the content of the component (A1) in the sunscreen cosmetic (2) of the present invention is 1 to 40% by mass, preferably 5 to 35% by mass, more preferably 10 to 30% by mass, and further preferably 15 to 25% by mass. The content of the component (A1) may be obtained as the total amount of the oil soluble ultraviolet ray absorbent (a1), the methylphenylpolysiloxane (a3) and the emulsifier.

The component (A1) may not exclude to contain the liquid oil agent (a2) other than the methylphenylpolysiloxane (a3) described for the oil-in-water type sunscreen cosmetic (1), but the content thereof is preferably small from the standpoint of the enhancement of the ultraviolet ray protection effect and the reduction of the sense of burden on the skin. The content of the liquid oil agent (a2) in the component (A1) is preferably less than 5% by mass, more preferably 2% by mass or less, further preferably 1% by mass or less, and still further preferably 0.1% by mass or less.

<Component (B)>

The component (B) contained in the sunscreen cosmetic (2) of the present invention and the preferred ranges thereof are the same as the component (B) in the oil-in-water type sunscreen cosmetic (1) except for the content thereof.

The content of the component (B) in the oil-in-water type sunscreen cosmetic (2) is 0.3% by mass or more, preferably 0.5% by mass or more, more preferably 0.7% by mass or more, further preferably 1% by mass or more, and still further preferably 2% by mass or more, and may be more than 2.5% by mass, from the standpoint of the uniformity and the water resistance of the coating film. The content thereof is 5% by mass or less, preferably 4.5% by mass or less, and more preferably 4% by mass or less, from the standpoint of the uniformity of the coating film and the less sense of burden on the skin. The specific range of the content of the component (B) in the sunscreen cosmetic (2) is 0.3 to 5% by mass, preferably 0.5 to 4.5% by mass, more preferably 0.7 to 4.5% by mass, further preferably 1 to 4.5% by mass, still further preferably 2 to 4.5% by mass, and still more further preferably more than 2.5% by mass and 4% by mass or less.

The content ratio of the component (A1) and the component (B) in the sunscreen cosmetic (2) of the present invention in terms of mass ratio (A1)/(B) is preferably 0.2 or more, more preferably 0.5 or more, further preferably 1 or more, and still further preferably 3 or more, from the standpoint of the uniformity and the water resistance of the coating film, and is preferably 50 or less, more preferably 40 or less, further preferably 30 or less, still further preferably 20 or less, and still more further preferably 10 or less, from the same standpoint. The specific range of the mass ratio (A1)/(B) is preferably 0.2 to 50, more preferably 0.5 to 40, further preferably 1 to 30, still further preferably 1 to 20, and still more further preferably 3 to 10.

The aqueous medium, the other components, and the preferred ranges thereof used in the sunscreen cosmetic (2) of the present invention are the same as in the oil-in-water type sunscreen cosmetic (1).

The production method of the oil-in-water type sunscreen cosmetic (2) is the same as in the oil-in-water type sunscreen cosmetic (1) except that the component (A) is replaced by the component (A1), and the oil soluble ultraviolet ray absorbent (a1) is replaced by the oil soluble ultraviolet ray absorbent (a1) and the methylphenylpolysiloxane (a3).

In relation to the aforementioned embodiments, the present invention further discloses to the following compositions.

<1> An oil-in-water type sunscreen cosmetic containing the following component (A) and the following component (B):
(A) 1% by mass or more and 40% by mass or less of emulsion particles containing an oil soluble ultraviolet ray absorbent (a1), having an average particle diameter of more than 6 μm and 300 μm or less, and
(B) 0.3% by mass or more and 2.5% by mass or less of particles containing an oil soluble ultraviolet ray absorbent (b3) encompassed by an ionic surfactant (b1) and a hydrophobic amphiphilic substance (b2), having a content of a solid oil agent of 2.5% by mass or less based on the total amount of the particles, having an average particle diameter of 6 μm or less.

<2> An oil-in-water type sunscreen cosmetic containing the following component (A1) and the following component (B):
(A) 1% by mass or more and 40% by mass or less of emulsion particles containing an oil soluble ultraviolet ray absorbent (a1) and a methylphenylpolysiloxane (a3), having an average particle diameter of more than 6 μm and 300 μm or less, and
(B) 0.3% by mass or more and 5% by mass or less of particles containing an oil soluble ultraviolet ray absorbent (b3) encompassed by an ionic surfactant (b1) and a hydrophobic amphiphilic substance (b2), having a content of a solid oil agent of 2.5% by mass or less based on the total amount of the particles, having an average particle diameter of 6 μm or less.

<3> The oil-in-water type sunscreen cosmetic according to the item <1>, wherein the content of the component (B) is preferably 0.5% by mass or more and 2% by mass or less, more preferably 0.7% by mass or more and 1.5% by mass or less, and further preferably 0.7% by mass or more and 1.2% by mass or less.

<4> The oil-in-water type sunscreen cosmetic according to the item <2>, wherein the content of the component (B) is preferably 0.5% by mass or more and 4.5% by mass or less, more preferably 0.7% by mass or more and 4.5% by mass or less, further preferably 1% by mass or more and 4.5% by mass or less, still further preferably 2% by mass or more and 4.5% by mass or less, and still more further preferably 2.5% by mass or more and 4% by mass or less.

<5> The oil-in-water type sunscreen cosmetic according to any one of the items <1> to <4>, wherein the average particle diameter of the component (A) or the component (A1) is preferably 10 μm or more and 200 μm or less, more preferably 10 μm or more and 100 μm or less, and further preferably 15 μm or more and 50 μm or less.

<6> The oil-in-water type sunscreen cosmetic according to any one of the items <1> to <5>, wherein the content of the component (A) or the component (A1) is preferably 5% by mass or more and 35% by mass or less, more preferably 10% by mass or more and 30% by mass or less, and further preferably 15% by mass or more and 25% by mass or less.

<7> The oil-in-water type sunscreen cosmetic according to any one of the items <1> to <6>, wherein the ionic surfactant (b1) is preferably an anionic surfactant, and more preferably a long-chain N-acylglutamate salt.

<8> The oil-in-water type sunscreen cosmetic according to any one of the items <1> to <7>, wherein the hydrophobic amphiphilic substance (b2) contains an alcohol having 14 or more and 22 or less carbon atoms, a monoglycerin ester of a fatty acid having 14 or more and 22 or less carbon atoms, and a sorbitan ester of a fatty acid having 14 or more and 22 or less carbon atoms.

<9> The oil-in-water type sunscreen cosmetic according to any one of the items <1> to <8>, wherein the hydrophobic amphiphilic substance (b2) contains cetyl alcohol, glycerin monobehenate, and sorbitan distearate.

<10> The oil-in-water type sunscreen cosmetic according to any one of the items <1> to <9>, wherein the content of the solid oil agent with respect to the component (B) is preferably 1% by mass or less, more preferably 0.1% by mass or less, and further preferably substantially 0% by mass.

<11> The oil-in-water type sunscreen cosmetic according to any one of the items <1> to <10>, wherein the component (B) is particles having an α-gel structure.

<12> The oil-in-water type sunscreen cosmetic according to any one of the items <1> to <11>, wherein the average particle diameter of the particles as the component (B) is preferably 0.05 μm or more and 6 μm or less, more preferably 0.08 μm or more and 3 μm or less, further preferably 0.1 μm or more and 1 μm or less, and still further preferably 0.1 μm or more and 0.3 μm or less.

<13> The oil-in-water type sunscreen cosmetic according to any one of the items <1> and <3> to <12>, wherein the content ratio of the component (A) and the component (B) in terms of mass ratio (A)/(B) is preferably 5 or more and 50 or less, more preferably 10 or more and 40 or less, and further preferably 15 or more and 30 or less.

<14> An oil-in-water type sunscreen cosmetic containing the following component (A) and the following component (B):
(A) 1% by mass or more and 40% by mass or less of emulsion particles containing an oil soluble ultraviolet ray absorbent (a1), having an average particle diameter of 10 μm or more and 100 μm or less, and
(B) 0.3% by mass or more and 2.5% by mass or less of particles containing an oil soluble ultraviolet ray absorbent (b3) encompassed by an ionic surfactant (b1) and a hydrophobic amphiphilic substance (b2), having a content of a solid oil agent of 2.5% by mass or less based on the total amount of the particles, having an average particle diameter of 0.1 μm or more and 1 μm or less.

<15> An oil-in-water type sunscreen cosmetic containing the following component (A1) and the following component (B):
(A1) 1% by mass or more and 40% by mass or less of emulsion particles containing an oil soluble ultraviolet ray absorbent (a1) and a methylphenylpolysiloxane (a3), having an average particle diameter of 10 μm or more and 100 μm or less, and
(B) 0.3% by mass or more and 5% by mass or less of particles containing an oil soluble ultraviolet ray absorbent (b3) encompassed by an ionic surfactant (b1) and a hydrophobic amphiphilic substance (b2), having a content of a solid oil agent of 2.5% by mass or less based on the total amount of the particles, having an average particle diameter of 0.1 μm or more and 1 μm or less.

<16> The oil-in-water type sunscreen cosmetic according to the item <14> or <15>, wherein the ionic surfactant (b1) is a long-chain N-acylglutamate salt.

<17> The oil-in-water type sunscreen cosmetic according to any one of the items <14> to <16>, wherein the hydrophobic amphiphilic substance (b2) contains an alcohol having 14 or more and 22 or less carbon atoms, a monoglycerin ester of a fatty acid having 14 or more and 22 or less carbon atoms, and a sorbitan ester of a fatty acid having 14 or more and 22 or less carbon atoms.

<18> The oil-in-water type sunscreen cosmetic according to any one of the items <14> to <17>, wherein the component (B) is particles having an α-gel structure.

<19> The oil-in-water type sunscreen cosmetic according to any one of the items <14> and <16> to <18>, wherein the content ratio of the component (A) and the component (B) in terms of mass ratio (A)/(B) is 5 or more and 50 or less.

<20> A method for producing an oil-in-water type sunscreen cosmetic, including the following steps (I) to (III):
step (I): emulsifying an oil phase containing an oil soluble ultraviolet ray absorbent (a1) in an aqueous medium with an emulsifier, so as to provide an emulsion containing emulsion particles (A) having an average particle diameter of more than 6 μm and 300 μm or less,
step (II): mixing an ionic surfactant (b1), a hydrophobic amphiphilic substance (b2), an oil soluble ultraviolet ray absorbent (b3), and an aqueous medium under heating for emulsifying, and then cooling at a cooling rate of 0.5° C./sec or more and 10° C./sec or less, so as to provide an emulsion containing particles (B) containing the component (b3) encompassed by the components (b1) and (b2), having an average particle diameter of 6 μm or less, and
step (III): mixing the emulsion containing the emulsion particles (A) obtained in the step (I) and the emulsion containing the particles (B) obtained in the step (II).

EXAMPLES

The present invention will be described with reference to examples below, but the present invention is not limited to the scope of the examples. In the examples, various measurements and evaluations were performed according to the following manner.

(Average Particle Diameter)

The average particle diameter (median diameter: D50) of particles was measured as a relative refractive index 1.200-0.000 i with water as a dispersion medium at 25° C. with a laser diffraction-scattering particle diameter distribution analyzer "LA-920", produced by Horiba, Ltd.

(Uniformity of Coating Film (CV Value))

The cosmetic of the example was uniformly coated on a polymethyl methacrylate (PMMA) plate of 5 cm×5 cm to make 2 mg/cm$^2$ over 1 minute, and dried at 25° C. for 15 minutes.

The absorbance at a wavelength of 307 nm was measured on the square PMMA plate at 9 points, i.e., the center, the vertexes (4 points), and the middle points of the four edges (4 points) with an SPF analyzer ("SPF 290S plus" produced by Optometrics LLC), and the CV value (standard deviation/average value) was obtained from the average value and the standard deviation of the absorbance, and was designated as the index of the uniformity of the coating film. A smaller CV value means better uniformity of the coating film.

(Water Resistance)

The cosmetic of the example was uniformly coated on a polymethyl methacrylate (PMMA) plate of 5 cm×5 cm to make 2 mg/cm$^2$ over 1 minute, and dried at 25° C. for 15 minutes.

The absorbance at a wavelength of 307 nm was measured on the square PMMA plate at 9 points, i.e., the center, the vertexes (4 points), and the middle points of the four edges (4 points) with an SPF analyzer ("SPF 290S plus" produced by Optometrics LLC), and the average value of the 9 points was obtained (which was designated as the initial average absorbance).

The PMMA plate was immersed in water at 30° C. for 20 minutes, allowed to stand in the air for 15 minutes, further immersed in water at 30° C. for 20 minutes (i.e., immersed in water for 40 minutes in total), and then dried for 15 minutes, and then the absorbance was again measured with the SPF analyzer in the same manner as above, from which the average value of the 9 points was obtained (which was designated as the average absorbance after water immersion). The ratio (N) of the average absorbance after water immersion with respect to the initial average absorbance was designated as the water resistance. A larger value thereof means higher water resistance.

(Absence of Sense of Burden)

The absence of sense of burden in use of the cosmetic of the example was subjected to sensory evaluation by 10 expert panelists, and evaluated by the following standard.

A: 10 panelists evaluated as no sense of burden.
B: 7 to 9 panelists evaluated as no sense of burden.
C: 4 to 6 panelists evaluated as no sense of burden.
D: 1 to 3 panelists evaluated as no sense of burden.
E: No panelist evaluated as no sense of burden.

Production Example 1

(Production of Component (A))

The components constituting the component (A) mixed in the mixing ratio shown in Table 1 and water in the mixing ratio shown in Table 3 were added to a 2 L vessel, and mixed under heating to 85° C. at 7,000 times for 3 minutes with an agihomomixer ("Labolution (A-TYPE)", produced by Primix Corporation), so as to provide an emulsion containing the component (A) (step (I)). The average particle diameter of the emulsion particles as the component (A) was 20 Jim.

The composition of the component (A) is shown in Table 1. The mixing amounts shown in Table 1 are the active ingredient amounts (% by mass) of the respective components.

TABLE 1

| Component | | | Production Example 1 (% by mass) |
|---|---|---|---|
| Component constituting component (A) | (a1) | 2-Ethylhexyl p-methoxycinnamate *1 | 57.6 |
| | | Hexyl diethylaminohydroxy-benzoylbenzoate *2 | 13.6 |
| | | bis(Ethylhexyloxyphenol) methoxyphenyltriazine *3 | 3.4 |
| | | Ethylhexyltriazone *4 | 13.6 |

TABLE 1-continued

| Component | | Production Example 1 (% by mass) |
|---|---|---|
| (a2) | Alkyl (C12-15) benzoate *5 | 11.5 |
| Emulsifier | Polyoxyethylene 2-hexyldecyl ether *6 | 0.3 |
| | Total | 100 |
| | Content of (a1) with respect to (a1) + (a2) | 88.5 |

The components in Table 1 are as follows.
*1: 2-Ethylhexyl p-methoxycinnamate, Uvinul MC80 (produced by BASF SE)
*2: Hexyl diethylaminohydroxybenzoylbenzoate, Uvinul Aplus Glanular (produced by BASF SE)
*3: bis(Ethylhexyloxyphenol)methoxyphenyltriazine, Tinosorb S (produced by BASF SE)
*4: Ethylhexyltriazone, Uvinul T-150 (produced by BASF SE)
*5: Alkyl (C12-15) benzoate, Finsolv TN (produced by Innospec Active Chemicals, LLC)
*6: Polyoxyethylene 2-hexyldecyl ether, Emulgen 1620G (produced by Kao Corporation)

Production Example 2

(Production of α-Gel Particles 1)

All the components described for Production Example 2 in Table 2 were dispersed under heating to 85° C. with an agihomomixer, and then treated with a high pressure emulsifier ("Econizer Labo-02", produced by Sanmaru Machinery Co., Ltd.) under condition of a pressure of 50 MPa and a number of pass of 1, so as to provide an emulsion. The resulting emulsion retained at 85° C. was fed to a vibration agitation mixing equipment ("Vibro Mixer", produced by Reica Co., Ltd.) over a transfer time of 10 seconds, and continuously cooled to 40° C. or less at a cooling rate of 5° C./sec under agitation of the emulsion through the vertical vibration of the agitation body in the equipment, so as to provide an emulsion containing α-gel particles 1 as the component (B), having the component (b3) encompassed by the components (b1) and (b2) (step (II)). The composition, the average particle diameter, and the content of the α-gel particles 1 are shown in Table 2. The mixing amounts shown in Table 2 are the active ingredient amounts (% by mass) of the respective components.

Production Examples 3 to 6 and Comparative Production Example 1

(Production of α-Gel Particles 2 to 6)

Emulsions containing α-gel particles 2 to 6 were produced in the same manner as in Production Example 2 except that the composition shown in Table 2 was used, and the average particle diameter of the particles in the emulsion was controlled by changing the pressure condition of the high pressure emulsifier as follows (step (II)).

| Pressure (MPa) | Average particle diameter (μm) |
|---|---|
| 0 | 6.0 |
| 10 | 0.5 |
| 50 | 0.2 |

The compositions of the emulsions, and the average particle diameter and the content of the α-gel particles are shown in Table 2.

The α-gel particles 6 obtained in Comparative Production Example 1 did not correspond to the component (B) since the particles contained ceresin and paraffin wax as the solid oil agent in an amount exceeding 2.5% by mass based on the total amount of the α-gel particles (which is referred to as the "component (B')" in the following description).

TABLE 2

|  |  | Component (% by mass) | Production Example 2 α-Gel particles 1 | Production Example 3 α-Gel particles 2 | Production Example 4 α-Gel particles 3 | Production Example 5 α-Gel particles 4 | Production Example 6 α-Gel particles 5 | Comparative Production Example 1 α-Gel particles 6 |
|---|---|---|---|---|---|---|---|---|
| Emulsion obtained in step (II) | (b1) | N-Stearoyl-L-glutamic acid *1 | 0.6 | 0.6 | 0.6 | 0.6 | 0.6 | 0.6 |
|  | (b2) | Cetyl alcohol *2 | 0.9 | 0.9 | 0.9 | 0.9 | 0.9 | 0.9 |
|  |  | Glycerin monobehenate *3 | 1.35 | 1.35 | 1.35 | 1.35 | 1.35 | 1.35 |
|  |  | Sorbitan distearate *4 | 0.75 | 0.75 | 0.75 | 0.75 | 0.75 | 0.75 |
|  | (b3) | 2-Ethylhexyl p-methoxycinnamate *5 | 9 | 8.5 | 8.5 | 9 | 9 | 9 |
|  |  | Hexyl cliethylaminohydroxybenzoylbenzoate *6 | 2 | 1.2 | 2 | 2 | 2 | 2 |
|  |  | bis(Ethylhexyloxyphenol) methoxyphenyltriazine *7 | 1 | 1.5 | 0.5 | 1 | 1 | 1 |
|  |  | Ethylhexyltriazone *8 | 0 | 0.5 | 2 | 0 | 0 | 0 |
|  | (b4) | Alkyl (C12-15) benzoate *9 | 3 | 0 | 0 | 3 | 3 | 3 |
| Solid oil agent |  | Ceresin *10 | 0 | 0 | 0 | 0 | 0 | 0.47 |
|  |  | Paraffin wax *11 | 0 | 0 | 0 | 0 | 0 | 0.53 |
| Other component |  | Phenoxyethanol *12 | 0.4 | 0.4 | 0.4 | 0.4 | 0.4 | 0.4 |
|  |  | Arginine | 0.33 | 0.33 | 0.33 | 0.33 | 0.33 | 0.33 |
|  |  | Propanediol | 2 | 2 | 2 | 2 | 2 | 2 |
|  |  | Glycerin | 2.58 | 2.58 | 2.58 | 2.58 | 2.58 | 2.58 |
|  |  | Water | balance | balance | balance | balance | balance | balance |
| Total |  |  | 100 | 100 | 100 | 100 | 100 | 100 |
| Content of emulsion particles (component (B) or component (B')) (% by mass) |  |  | 18.6 | 15.3 | 16.6 | 18.6 | 18.6 | 19.6 |
| Content of solid oil agent based on emulsion particles (component (B) or component (B')) (% by mass) |  |  | 0 | 0 | 0 | 0 | 0 | 5.1 |
| Mass ratio b3/(b1 + b2) |  |  | 3.33 | 3.25 | 3.61 | 3.33 | 3.33 | 3.33 |
| Average particle diameter of component (B) or component (B') (μm) |  |  | 0.20 | 0.20 | 0.20 | 0.50 | 6.0 | 0.20 |

The components in Table 2 are as follows.
*1: N-Stearoyl-L-glutamic acid, Amisoft HA-P (produced by Ajinomoto Co., Inc.)
*2: Cetyl alcohol, Cetyl Alcohol NX (produced by Kokyu Alcohol Kogyo Co., Ltd.)
*3: Glycerin monobehenate, Sunsoft No. 8100-C (produced by Taiyo Kagaku Co., Ltd.)
*4: Sorbitan clistearate, Sunsoft No. 63C-C (produced by Taiyo Kagaku Co., Ltd.)
*5: 2-Ethylhexyl p-methoxycinnamate, Uvinul MC80 (produced by BASF SE)
*6: Hexyl diethylaminohydroxybenzoylbenzoate, Uvinul Aplus Glanular (produced by BASF SE)
*7: bis(Ethylhexyloxyphenol)methoxyphenyltriazine, Tinosorb S (produced by BASF SE)
*8: Ethylhexyltriazone, Uvinul T-150 (produced by BASF SE)
*9: Alkyl (C12-15) benzoate, Finsolv TN (produced by Innospec Active Chemicals, LLC)
*10: Ceresin, Ceresin #810K (produced by Nikko Rica Corporation), melting point: 74° C.
*11: Paraffin wax, HNP-9 (produced by Nippon Seiro Co., Ltd.), melting point: 75° C.
*12: Phenoxyethanol, Hisolve EPH (produced by Toho Chemical Industry Co., Ltd.)

Examples 1 to 9 and Comparative Examples 1 to 6

(Production and Evaluation of Oil-in-Water Type Sunscreen Cosmetic (1) and Comparative Oil-in-Water Type Sunscreen Cosmetic)

The emulsion containing the component (A) obtained in Production Example 1, the emulsion containing the component (B) or the component (B') obtained in Production Examples 2 to 6 or Comparative Production Example 1, an alkyl acrylate-methacrylate copolymer (*1 in Table 3, "Pemulen TR-1", produced by Lubrizol Advanced Materials, Inc.), and 48% KOH were mixed in the mixing ratio shown in Table 3 at room temperature (25° C.), so as to provide an oil-in-water type sunscreen cosmetic (1) and a comparative oil-in-water type sunscreen cosmetic (step III).

The resulting cosmetics were subjected to the evaluations by the methods described above. The results are shown in Table 3.

The SPF values of the oil-in-water type sunscreen cosmetics of Example 1 and Comparative Example 1 were 60 and 30, respectively. The SPF value was measured according to ISO 24444.

TABLE 3

| Component (% by mass) |  | Example 1 | 2 | 3 | 4 | 5 | 6 | 7 | 8 | 9 | Comparative Example 1 | 2 | 3 | 4 | 5 | 6 |
|---|---|---|---|---|---|---|---|---|---|---|---|---|---|---|---|---|
| Component (A) Water | Emulsion of Production Example 1 | 20 | 10 | 30 | 20 | 20 | 20 | 20 | 20 | 20 | 20 | — | 20 | 45 | 0.5 | 20 |
|  |  | 74.9 | 84.9 | 64.9 | 77.2 | 70.2 | 74.9 | 74.9 | 74.9 | 74.9 | 79.6 | 94.9 | 74.9 | 49.9 | 94.4 | 64.6 |
| Component (B) | Emulsion of Production Example 2 | 4.7 | 4.7 | 4.7 | 2.4 | 9.4 |  |  |  |  |  |  | 4.7 |  | 4.7 | 15 |
|  | Emulsion of Production Example 3 |  |  |  |  |  | 4.7 |  |  |  |  |  |  |  |  |  |

TABLE 3-continued

| Component (% by mass) | | Example 1 | 2 | 3 | 4 | 5 | 6 | 7 | 8 | 9 | Comparative Example 1 | 2 | 3 | 4 | 5 | 6 |
|---|---|---|---|---|---|---|---|---|---|---|---|---|---|---|---|---|
| Component (B') | Emulsion of Production Example 4 | | | | | | | 4.7 | | | | | | | | |
| | Emulsion of Production Example 5 | | | | | | | | 4.7 | | | | | | | |
| | Emulsion of Production Example 6 | | | | | | | | | 4.7 | | | | | | |
| | Emulsion of Comparative Production Example 1 | | | | | | | | | | | 4.7 | | | | |
| Alkyl acrylate-methacrylate copolymer *1 | | 0.2 | 0.2 | 0.2 | 0.2 | 0.2 | 0.2 | 0.2 | 0.2 | 0.2 | 0.2 | 0.2 | 0.2 | 0.2 | 0.2 | 0.2 |
| 48% KOH | | 0.2 | 0.2 | 0.2 | 0.2 | 0.2 | 0.2 | 0.2 | 0.2 | 0.2 | 0.2 | 0.2 | 0.2 | 0.2 | 0.2 | 0.2 |
| Total | | 100 | 100 | 100 | 100 | 100 | 100 | 100 | 100 | 100 | 100 | 100 | 100 | 100 | 100 | 100 |
| Content of component (A) (% by mass) | | 20 | 10 | 30 | 20 | 20 | 20 | 20 | 20 | 20 | 20 | — | 20 | 45 | 0.5 | 20 |
| Content of component (B) or (B') (% by mass) | | 0.87 | 0.87 | 0.87 | 0.45 | 1.75 | 0.72 | 0.78 | 0.87 | 0.87 | — | 0.87 | 0.92 | 0.87 | 0.87 | 2.8 |
| Average particle diameter of component (B) or (B') (μm) | | 0.20 | 0.20 | 0.20 | 0.20 | 0.20 | 0.20 | 0.20 | 0.50 | 6.0 | — | 0.20 | 0.20 | 0.20 | 0.20 | 0.20 |
| Mass ratio (A)/(B) | | 22.9 | 11.4 | 34.3 | 44.8 | 11.4 | 27.8 | 25.6 | 22.9 | 22.9 | — | — | — | 51.5 | 0.6 | 7.2 |
| Evaluation result | Uniformity of coating film (CV value) | 5 | 9 | 9 | 15 | 9 | 5 | 5 | 16 | 24 | 36 | 36 | 16 | 20 | 36 | 24 |
| | Water resistance (%) | 87 | 82 | 85 | 66 | 75 | 82 | 85 | 77 | 77 | 70 | 40 | 75 | 66 | 40 | 75 |
| | Absence of sense of burden | A | A | A | A | A | A | A | A | A | A | A | C | E | B | C |

It is understood from Table 3 that the oil-in-water type sunscreen cosmetic (1) of the present invention is excellent in uniformity and water resistance of the coating film and has a less sense of burden on the skin.

On the other hand, the sunscreen cosmetic of Comparative Example 1 containing no component (B) and the sunscreen cosmetic of Comparative Example 2 containing no component (A) were inferior in uniformity of the coating film, and Comparative Example 2 was inferior also in water resistance. The sunscreen cosmetic of Comparative Example 3 containing the component (B) containing the solid oil agent in an amount exceeding 2.5% by mass had a sense of burden on the skin and poor use feeling. Comparative Example 4 having a content of the component (A) exceeding 40% by mass, Comparative Example 5 having a content of the component (A) of less than 1% by mass, and Comparative Example 6 having a content of the component (B) exceeding 2.5% by mass all had poor use feeling, and Comparative Example 5 was inferior also in uniformity and water resistance of the coating film.

Production Example 7

(Production of Component (A1))

The components constituting the component (A1) mixed in the mixing ratio shown in Table 4 and water in the mixing ratio shown in Table 7 were added to a 2 L vessel, and mixed under heating to 85° C. at 7,000 times for 3 minutes with an agihomomixer ("Labolution (A-TYPE)", produced by Primix Corporation), so as to provide an emulsion containing the component (A1) (step (I)). The average particle diameter of the emulsion particles as the component (A1) was 20 μm.

The composition of the component (A1) is shown in Table 4. The mixing amounts shown in Table 4 are the active ingredient amounts (% by mass) of the respective components.

TABLE 4

| | | Component | Production Example 7 (% by mass) |
|---|---|---|---|
| Component constituting component (A1) | (a1) | Homomenthyl salicylate *13 | 38.3 |
| | | Octyl salicylate *14 | 19.2 |
| | | 4-tert-Butyl-4'-methoxydibenzoylmethane *15 | 11.5 |
| | | Octocrylene *16 | 19.2 |
| | (a3) | Phenyl trimethicone *17 | 11.5 |
| | Emulsifier | Polyoxyethylene 2-hexyldecyl ether *6 | 0.3 |
| | | Total | 100 |
| Content of (a1) with respect to (a1) + (a3) | | | 88.5 |

Production Example 8

(Production of Component (A))

The components constituting the component (A) mixed in the mixing ratio shown in Table 5 and water in the mixing ratio shown in Table 7 were added to a 2 L vessel, and mixed under heating to 85° C. at 7,000 times for 3 minutes with an agihomomixer ("Labolution (A-TYPE)", produced by Primix Corporation), so as to provide an emulsion containing the component (A) (step (I)). The average particle diameter of the emulsion particles as the component (A) was 20 μm.

The composition of the component (A) is shown in Table 5. The mixing amounts shown in Table 5 are the active ingredient amounts (% by mass) of the respective components.

TABLE 5

| Component | | | Production Example 8 (% by mass) |
|---|---|---|---|
| Component constituting component (A) | (a1) | Homomenthyl salicylate *13 | 38.3 |
| | | Octyl salicylate *14 | 19.2 |
| | | 4-tert-Butyl-4'-methoxydibenzoylmethane *15 | 11.5 |
| | | Octocrylene *16 | 19.2 |
| | (a2) | Alkyl (C12-15) benzoate *5 | 11.5 |
| | Emulsifier | Polyoxyethylene 2-hexyldecyl ether *6 | 0.3 |
| | | Total | 100 |
| | | Content of (a1) with respect to (a1) + (a2) | 88.5 |

The components in Tables 4 and 5 are as follows.
*6: Polyoxyethylene 2-hexyldecyl ether, Emulgen 1620G (produced by Kao Corporation)
*13: Homomenthyl salicylate, Parsol HMS (produced by DSM N.V.)
*14: Octyl salicylate, Parsol EHS (produced by DSM N.V.)
*15: 4-tert-Butyl-4'-methoxydibenzoylmethane, Parsol 1789 (produced by DSM N.V.)
*16: Octocrylene, Parsol 340 (produced by DSM N.V.)
*17: Phenyl trimethicone, Dowsil 556 Cosmetic Grade Fluid (produced by Dow Corning Toray Co., Ltd.)

Production Example 9

(Production of α-Gel Particles 7)

An emulsion containing α-gel particles 7 was produced in the same manner as in Production Example 2 using the composition shown in Table 6 (step (II)).

The composition of the emulsion and the average particle diameter and the content of the α-gel particles are shown in Table 6.

TABLE 6

| Component (% by mass) | | | Production Example 9 α-Gel particles 7 |
|---|---|---|---|
| Emulsion obtained in step (II) | (b1) | N-Stearoyl-L-glutamic acid *1 | 0.6 |
| | (b2) | Cetyl alcohol *2 | 0.9 |
| | | Glycerin monobehenate *3 | 1.35 |
| | | Sorbitan distearate *4 | 0.75 |
| | (b3) | Homomenthyl salicylate *13 | 6.4 |
| | | Octyl salicylate *14 | 3.2 |
| | | 4-tert-Butyl-4'-methoxydibenzoylmethane *15 | 1.9 |
| | | Octocrylene *16 | 3.2 |
| | (b4) | Alkyl (C12-15) benzoate *9 | 0 |
| | Solid oil agent | Ceresin *10 | 0 |
| | | Paraffin wax *11 | 0 |
| | Other component | Phenoxyethanol *12 | 0.4 |
| | | Arginine | 0.33 |
| | | Propanediol | 2 |
| | | Glycerin | 2.58 |
| | | Water | balance |
| | | Total | 100 |
| Content of emulsion particles (component (B)) (% by mass) | | | 18.3 |
| Content of solid oil agent based on emulsion particles (component (B)) (% by mass) | | | 0 |

TABLE 6-continued

| Component (% by mass) | Production Example 9 α-Gel particles 7 |
|---|---|
| Mass ratio b3/(b1 + b2) | 4.08 |
| Average particle diameter of component (B) (μm) | 0.20 |

The components in Table 6 are as follows.
*1: N-Stearoyl-L-glutamic acid, Amisoft HA-P (produced by Ajinomoto Co., Inc.)
*2: Cetyl alcohol, Cetyl Alcohol NX (produced by Kokyu Alcohol Kogyo Co., Ltd.)
*3: Glycerin monobehenate, Sunsoft No. 8100-C (produced by Taiyo Kagaku Co., Ltd.)
*4: Sorbitan distearate, Sunsoft No. 63C-C (produced by Taiyo Kagaku Co., Ltd.)
*9: Alkyl (C12-15) benzoate, Finsolv TN (produced by Innospec Active Chemicals, LLC)
*10: Ceresin, Ceresin #810K (produced by Nikko Rica Corporation), melting point: 74° C.
*11: Paraffin wax, HNP-9 (produced by Nippon Seiro Co., Ltd.), melting point: 75° C.
*12: Phenoxyethanol, Hisolve EPH (produced by Toho Chemical Industry Co., Ltd.)
*13: Homomenthyl salicylate, Parsol HMS (produced by DSM N.V.)
*14: Octyl salicylate, Parsol EHS (produced by DSM N.V.)
*15: 4-tert-Butyl-4'-methoxydibenzoylmethane, Parsol 1789 (produced by DSM N.V.)
*16: Octocrylene, Parsol 340 (produced by DSM N.V.)

Example 10 and Comparative Example 7

(Production and Evaluation of Oil-in-Water Type Sunscreen Cosmetic (2) and Comparative Oil-in-Water Type Sunscreen Cosmetic)

The emulsion containing the component (A1) or the component (A) obtained in Production Example 7 or 8, the emulsion containing the component (B) obtained in Production Example 9, an alkyl acrylate-methacrylate copolymer (*1 in Table 7, "Pemulen TR-1", produced by Lubrizol Advanced Materials, Inc.), and 48% KOH were mixed in the mixing ratio shown in Table 7 at room temperature (25° C.), so as to provide an oil-in-water type sunscreen cosmetic (2) and a comparative oil-in-water type sunscreen cosmetic (step III).

The resulting cosmetics were subjected to the evaluations by the methods described above. The results are shown in Table 7.

TABLE 7

| Component (% by mass) | | Example 10 | Comparative Example 7 |
|---|---|---|---|
| Component (A1) Water | Emulsion of Production Example 7 | 20 59.6 | |
| Component (A) Water | Emulsion of Production Example 8 | | 20 59.6 |
| Component (B) | Emulsion of Production Example 9 | 20 | 20 |
| Alkyl acrylate-methacrylate copolymer *1 | | 0.2 | 0.2 |
| 48% KOH | | 0.2 | 0.2 |
| Total | | 100 | 100 |
| Content of component (A) or (A1) (% by mass) | | 20 | 20 |
| Content of component (B) (% by mass) | | 3.66 | 3.66 |
| Average particle diameter of component (B) (μm) | | 0.20 | 0.20 |
| Mass ratio (A1)/(B) | | 5.5 | 0 |
| Mass ratio (A)/(B) | | 0 | 5.5 |
| Evaluation result | Uniformity of coating film (CV value) | 9 | 11 |
| | Water resistance (%) | 79 | 75 |
| | Absence of sense of burden | A | C |

INDUSTRIAL APPLICABILITY

The oil-in-water type sunscreen cosmetic of the present invention can provide a coating film excellent in uniformity and water resistance, can provide an excellent ultraviolet ray protection effect, and has a less sense of burden on the skin and good use feeling thereon.

The invention claimed is:

1. An oil-in-water type sunscreen cosmetic, comprising the following component (A) and the following component (B):
  (A) 1% by mass or more and 40% by mass or less of emulsion particles comprising an oil soluble ultraviolet ray absorbent (a1), wherein the emulsion particles have an average particle diameter of more than 6 μm and 300 μm or less, and
  (B) 0.3% by mass or more and 2.5% by mass or less of particles comprising an oil soluble ultraviolet ray absorbent (b3) encompassed by an ionic surfactant (b1) and a hydrophobic amphiphilic substance (b2), wherein the particles have a content of a solid oil agent of 2.5% by mass or less based on a total amount of the particles, and an average particle diameter of 6 μm or less.

2. The oil-in-water type sunscreen cosmetic according to claim 1, wherein the ionic surfactant (b1) is an anionic surfactant.

3. The oil-in-water type sunscreen cosmetic according to claim 1, wherein the hydrophobic amphiphilic substance (b2) comprises an alcohol having 14 or more and 22 or less carbon atoms, a monoglycerin ester of a fatty acid having 14 or more and 22 or less carbon atoms, and a sorbitan ester of a fatty acid having 14 or more and 22 or less carbon atoms.

4. The oil-in-water type sunscreen cosmetic according to claim 1, wherein the component (B) is particles having an α-gel structure.

5. A method for producing an oil-in-water type sunscreen cosmetic, the method comprising:
  emulsifying an oil phase containing an oil soluble ultraviolet ray absorbent (a1) in an aqueous medium with an emulsifier, so as to provide an emulsion containing emulsion particles (A) having an average particle diameter of more than 6 μm and 300 μm or less,
  mixing an ionic surfactant (b1), a hydrophobic amphiphilic substance (b2), an oil soluble ultraviolet ray absorbent (b3), and an aqueous medium under heating for emulsifying, and then cooling at a cooling rate of 0.5° C./sec or more and 10° C./sec or less, so as to provide an emulsion containing particles (B) containing the component (b3) encompassed by the components (b1) and (b2), having an average particle diameter of 6 μm or less, and
  mixing the emulsion containing the emulsion particles (A) and the emulsion containing the particles (B).

6. An oil-in-water type sunscreen cosmetic, comprising the following component (A1) and the following component (B):
  (A1) 1% by mass or more and 40% by mass or less of emulsion particles containing an oil soluble ultraviolet ray absorbent (a1) and a methylphenylpolysiloxane (a3), wherein the emulsion particles have an average particle diameter of more than 6 μm and 300 μm or less, and
  (B) 0.3% by mass or more and 5% by mass or less of particles containing an oil soluble ultraviolet ray absorbent (b3) encompassed by an ionic surfactant (b1) and a hydrophobic amphiphilic substance (b2), wherein the particles have a content of a solid oil agent of 2.5% by mass or less based on a total amount of the particles, and an average particle diameter of 6 μm or less.

* * * * *